(12) United States Patent
Brostrom et al.

(10) Patent No.: US 10,966,937 B2
(45) Date of Patent: Apr. 6, 2021

(54) COMPOSITIONS AND METHODS FOR DELIVERY OF POLYUNSATURATED FATTY ACID DERIVATIVES AND ANALOGS

(71) Applicant: Cytometix, Inc., Bayside, WI (US)

(72) Inventors: Lane Brostrom, Bayside, WI (US); Henry Bordas-Murphy, Wauwatosa, WI (US); John R. Falck, Dallas, TX (US)

(73) Assignee: Cytometix, Inc., Milwaukee, WI (US)

( * ) Notice: Subject to any disclaimer, the term of this patent is extended or adjusted under 35 U.S.C. 154(b) by 0 days.

(21) Appl. No.: 15/571,314

(22) PCT Filed: May 3, 2016

(86) PCT No.: PCT/US2016/030503
§ 371 (c)(1),
(2) Date: Nov. 2, 2017

(87) PCT Pub. No.: WO2016/179137
PCT Pub. Date: Nov. 10, 2016

(65) Prior Publication Data
US 2018/0280318 A1  Oct. 4, 2018

Related U.S. Application Data

(60) Provisional application No. 62/156,444, filed on May 4, 2015.

(51) Int. Cl.
| | |
|---|---|
| *A61K 45/06* | (2006.01) |
| *A61K 9/48* | (2006.01) |
| *A61K 31/202* | (2006.01) |
| *A61P 29/00* | (2006.01) |
| *A61K 31/05* | (2006.01) |
| *A61K 31/164* | (2006.01) |
| *A61K 31/4468* | (2006.01) |
| *A61K 31/381* | (2006.01) |
| *A61K 31/135* | (2006.01) |
| *A61K 31/16* | (2006.01) |
| *A61K 31/197* | (2006.01) |

(52) U.S. Cl.
CPC ............ *A61K 31/05* (2013.01); *A61K 9/4825* (2013.01); *A61K 9/4858* (2013.01); *A61K 9/4891* (2013.01); *A61K 31/135* (2013.01); *A61K 31/16* (2013.01); *A61K 31/164* (2013.01); *A61K 31/197* (2013.01); *A61K 31/202* (2013.01); *A61K 31/381* (2013.01); *A61K 31/4468* (2013.01); *A61K 45/06* (2013.01); *A61P 29/00* (2018.01)

(58) Field of Classification Search
None
See application file for complete search history.

(56) References Cited

U.S. PATENT DOCUMENTS

| | | | | |
|---|---|---|---|---|
| 2007/0036862 A1* | 2/2007 | Rongen | ................ | A61K 9/4808 424/472 |
| 2007/0212411 A1* | 9/2007 | Fawzy | ................ | A61K 9/4808 424/457 |
| 2011/0158983 A1* | 6/2011 | Bascomb | ............ | A61K 31/138 424/133.1 |
| 2011/0280852 A1* | 11/2011 | Miller | ..................... | A23L 33/15 424/94.1 |
| 2012/0010280 A1* | 1/2012 | Aleo | ..................... | A61K 9/0048 514/458 |
| 2013/0023510 A1* | 1/2013 | Brostrom | .............. | C07C 233/09 514/183 |
| 2013/0108696 A1* | 5/2013 | Berge | ....................... | A61K 9/28 424/456 |
| 2013/0295173 A1* | 11/2013 | Machielse | ............ | A61K 31/505 424/463 |
| 2014/0017308 A1* | 1/2014 | Hustvedt | .............. | A61K 9/1075 424/456 |

FOREIGN PATENT DOCUMENTS

WO   WO-2013072767 A1 *  5/2013 ............. A61K 47/10

\* cited by examiner

*Primary Examiner* — Kyung S Chang
(74) *Attorney, Agent, or Firm* — Boyle Fredrickson, S.C.

(57) ABSTRACT

The present invention provides a system enabling the oral delivery of therapeutics derived from polyunsaturated fatty acids (PUFAs), their metabolites and derivatives, including, eicosanoids, prostaglandins, prostacyclins, leukotrienes, resolvins, endocannabinoids, thromboxanes, epoxyeicosatrienoic acids (EETs), hydroxyeicostetraenoic acids (HETEs), and CMX-020. The delivery system includes a vehicle comprising a purified docosahexaenoic acid (DHA) in triglyceride or ester form; a purified eicosapentaenoic acid (EPA) in triglyceride or ester form; a combination of DHA, EPA in either triglyceride or ester forms; or a modified DHA, EPA, or omega-3 fatty acid analog; and optionally, an antioxidant, a surfactant, a solubilizer, a stabilizer, a lubricant, or a pH/tonicity adjustment agent.

8 Claims, 22 Drawing Sheets

Outer shell contains new drug which dissolves in the stomach

Inner shell has enteric coating and conatins CMX20/fish oil this side enteric coated dissolves in stomach COMPOSITIONS AND METHODS FOR DELIVERY OF POLYUNSATURATED FATTY ACID DERIVATIVES AND ANALOGS

CROSS-REFERENCE TO RELATED APPLICATIONS

This International application claims the benefit of U.S. Provisional application 62/156,444, filed May 4, 2015, which is incorporated by reference herein in its entirety for all purposes.

STATEMENT REGARDING FEDERALLY SPONSORED RESEARCH OR DEVELOPMENT

Not Applicable.

FIELD OF THE INVENTION

This invention describes a new system for the oral delivery of drug products that are derived from, contain, resemble, or are analogs of polyunsaturated lipids, especially polyunsaturated fatty acids (PUFAs) such as linolenic, arachidonic, eicosapentaenoic, docosahexaenoic acids, and include eicosanoids, oxylipins, prostaglandins, leukotrienes, lipoxins, resolvins, protectins, hepoxilins, trioxilins, endocannabinoids, epoxyeicosa-trienoic acids (EETs), hydroxyeicostetraenoic acids (HETEs), and their chemical derivatives as well as analogs.

BACKGROUND OF THE INVENTION

Arachidonic acid (AA) is a 20 carbon polyunsaturated omega-6 fatty acid present in the phospholipid membranes of cells and is abundant in the brain, muscle, and liver. AA is involved in cellular signaling as a lipid second messenger in the regulation of signaling enzymes, such as PLC-γ, PLC-δ, and PKC-α, -β, and -γ isoforms; it is also a key inflammatory intermediate and can also act as a vasodilator. AA is essential to the repair and growth of skeletal muscle tissue. It is one of the most abundant fatty acids in the brain, it is involved in early neurological development and neurological health is reliant upon sufficient levels of AA.

In adults, the disturbed metabolism of AA contributes to neurological disorders such as Alzheimer's disease and bipolar disorder. This involves significant alterations in the conversion of AA to other bioactive molecules. As it is a precursor for other bioactive lipid molecules and the production of eicosanoids, the production of these derivatives and their action in the body are collectively known as the "arachidonic acid cascade".

In biochemistry, eicosanoids are signaling molecules made by oxidation of 20-carbon fatty acids. They exert complex control over many bodily systems; in growth during and after physical activity, inflammation or immunity after the intake of toxic compounds and pathogens, and as modulators and messengers in the central nervous system. The networks of controls that depend upon eicosanoids are among the most complex in the human body. See Gilman et al., eds., Goodman and Gilman's The Pharmacological Basis of Therapeutics, Eighth Edition, Pergamon Press. New York, pp. 600-611 (1990), incorporated herein by reference, for a more complete discussion of the structure and synthesis of the eicosanoids, including the prostaglandins, prostacyclins, thromboxanes and leukotrienes.

AA and its analogs are subject to metabolic and chemical oxidation, acidic degradation, poor solubility, low bioavailability, fast metabolism in the liver and elsewhere, and short half-lives. There are many different commercial delivery vehicles that can and have been used for delivering lipid therapeutics. These include a wide variety of oil suspensions, emulsions, liposomes, self-micro or self-nano emulsifying drug delivery systems (SMEDDS/SNEDDS). Lipid-based delivery vehicles include single oil solutions, complex mixtures of oils, co-solvents, and surfactants. While these and other various classes of lipid based vehicles have been developed to address or enhance systemic exposure of small lipophilic compounds following oral delivery, the results for AA chemistries provide low bioavailability, short systemic half-lives, and a short shelf-life.

Alternatively, there are kits and precedents for development of liposomes, micelles, polymers, and other more complex nanocarriers, but these types of vehicles are also limited in bioavailability, provide short half-lives, or carry their own potential for adverse physiological effects. As a result, there has been only limited success in using commercial vehicles or developing more complex vehicles for delivering AA and its analogs, as demonstrated by the current absence of products on the market.

Accordingly, there remains a need for a novel delivery vehicle for AA and its analogs.

SUMMARY OF THE INVENTION

Here, the inventors demonstrate a novel use for highly purified docosahexaenoic acid (DHA) or eicosapentaenoic acid (EPA) in triglyceride form. The invention is based, in part, on the understanding that triglycerides composed of mainly DHA or EPA facilitate the stability, controlled release, absorption, transport, and decreased metabolism of polyunsaturated lipids administered via the oral route. The result provides increased bioavailability and longer exposure times as compared with other standard oily vehicles known to be bioavailability enhancers for highly lipophilic compounds.

Accordingly, the invention encompasses in a first aspect an oral delivery system having an enteric coated softgel; and a liquid formulation contained within the enteric coated softgel, the liquid formulation including a vehicle including a purified docosahexaenoic acid (DHA) in triglyceride or ester form; a purified eicosapentaenoic acid (EPA) in triglyceride or ester form; a combination of DHA, EPA in either triglyceride or ester forms; or a modified DHA, EPA, or omega 3 fatty acid analog; and optionally, one or more of an antioxidant, a surfactant, a solubilizer, a stabilizer, a lubricant, or a pH/tonicity adjustment agent.

The antioxidant may be selected from a group consisting of a mixed tocopherol, a pure tocopherol, a carotene, a propyl gallate, a butylated hydroxyltoluene (BHT), a butylated hydroxyanisole (BHA), and combinations thereof.

The vehicle may include a combination of about 20% to about 100% (w/w) DHA in triglyceride or ester form and about 20% to about 100% (w/w) EPA in triglyceride or ester form. For example, the vehicle may have a combination of about 50% (w/w) DHA in triglyceride form and about 32% (w/w) EPA in triglyceride form.

The liquid formulation may further include a therapeutic. The therapeutic may be a polyunsaturated fatty acid (PUFA), or a metabolite or derivative thereof. Alternatively, the therapeutic may be an eicosanoid, prostaglandin, prostacyclin, leukotriene, endocannabinoid, thromboxane, epoxyeicosatrienoic acid (EET), hydroxyeicosatetraenoic acids (HETE), or a metabolite or derivative thereof. Alternatively, the therapeutic may be arachidonic acid or a derivative thereof. Alternatively, the therapeutic may be an endogenous endocannabinoid anandamide or AM356 (R1 Meth-anandamide).

Alternatively, the therapeutic may be CMX-020. CMX-020 may be about 2-25% (w/w) of the liquid formulation. For example, CMX-020 may be about 5% (w/w) of the liquid formulation.

The composition may include a second therapeutic. The second therapeutic may be selected from the group consisting of an opioid, pregabalin, gabapentin, tramadol, serotonin-norepinephrine reuptake inhibitor (SNRI), tricyclic antidepressant (TCA), selective serotonin re-uptake inhibitor (SSRI), serotonin-norepinephrine releasing agent (SNRA), norepinephrine reuptake inhibitor (NRI), non-steroidal anti-inflammatory drug (NSAID), or a combination thereof. Alternatively, the second therapeutic may be selected from a group consisting of remifentanil, pregabalin, tramadol, duloxetine, or a combination thereof.

The second therapeutic may be contained in a non-enteric coated outer shell surrounding the enteric coated softgel. The outer shell may release the second therapeutic in a simulated gastric fluid test solution in less than about 2 hours.

The present invention further provides a method of delivering an effective dosage of a therapeutic to a patient, comprising administering an oral delivery system according to the oral delivery system described above to a patient, where an effective dosage of a therapeutic contained within the oral delivery system is delivered to said patient.

The therapeutic may treat pain, high blood pressure, high triglycerides, hyperlipidemia, coronary artery disease, obesity, nausea, sleep disorders, depression, anxiety disorders, or the symptoms thereof in the patient.

The invention further provides use of an oral delivery system described above for the manufacture of a medicament for orally-delivering a therapeutic to a patient.

The invention further provides an oral delivery system described above for use in orally-delivering a therapeutic to a patient.

The presently described and claimed compounds and methods described provide various advantages over prior methods in that they provide for increased systemic exposure, prolonged exposure time, a reduction of side effects, and dose encountered with standard oily delivery vehicles and single active ingredient formulations. In co-administration studies, CMX-020 displays a synergistic analgesic effect when combined with opioids, pregabalin, duloxetine and tramadol. Thus providing reduced drug dose of each therapeutic, potentially reduced side effect profiles, and increased efficacy during treatment.

Other objects, features and advantages of the present invention will become apparent after review of the specification, claims and drawings.

DETAILED DESCRIPTION OF THE INVENTION

I. In General

Figure 1:
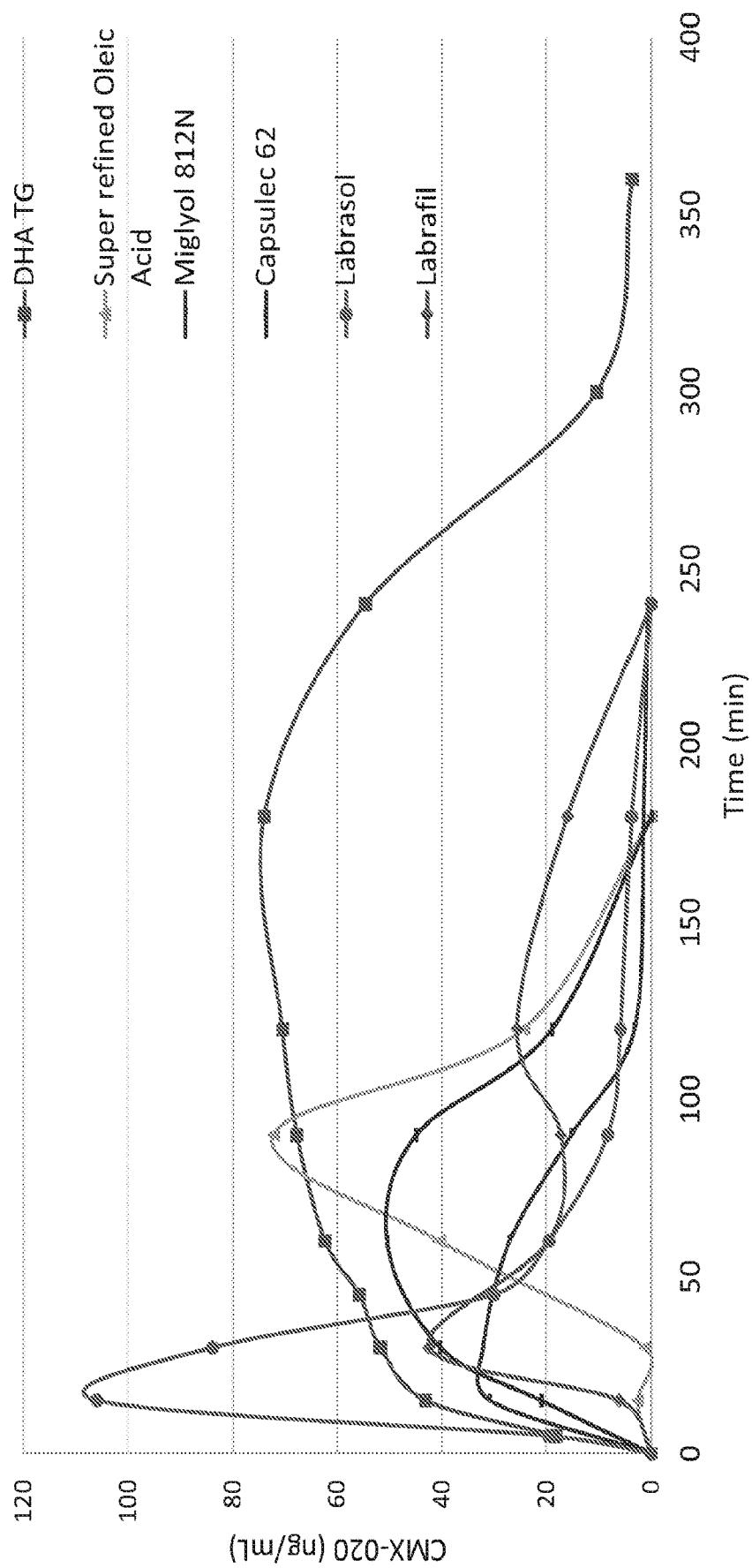
FIG. 1 is a graph showing concentration of CMX-020 measured over time when in various bioavailability enhancing vehicles.

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by any later-filed nonprovisional applications.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

As used herein, "subject" means mammals and non-mammals. "Mammals" means any member of the class Mammalia including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

As used herein, "administering" or "administration" includes any means for introducing a compound of the present invention into the body, preferably into the systemic circulation. Examples include but are not limited to oral, nasal, otic, ophthalmic, buccal, sublingual, pulmonary, transdermal, transmucosal, as well as subcutaneous, intraperitoneal, intravenous, epidural and intramuscular injection.

A "therapeutically effective amount" means an amount of a compound that, when administered to a subject for treating a disorder, condition, or disease, is sufficient to effect such treatment for the disorder, or condition, or disease. The "therapeutically effective amount" will vary depending on the compound, the disorder, or condition, or disease state being treated, the severity or the disorder, or condition, or disease treated, the age and relative health of the subject, the route and form of administration, the judgment of the attending medical or veterinary practitioner, and other factors.

For purposes of the present invention, "treating" or "treatment" describes the management and care of a patient for the purpose of combating the disease, condition, or disorder. The terms embrace both preventative, i.e., prophylactic, and palliative treatments. Treating includes the administration of a compound of present invention to prevent the onset of the symptoms or complications, alleviating the symptoms or complications, or eliminating the disease, condition, or disorder.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

II. The Invention

The current invention is the composition of a delivery vehicle that enables oral delivery of therapeutics derived from PUFAs, their metabolites and derivatives, including, eicosanoids, prostaglandins, prostacyclins, leukotrienes, endocannabinoids, thromboxanes, resolvins, EETs, and HETEs. An exemplary therapeutic for delivery is the molecule designated CMX-020.

Enzymatically produced metabolites of PUFAs are myriad, and are present in most cells, interstitial cellular space, and body fluids. These metabolites typically activate specific cellular receptors that trigger physiological actions and/or maintain dynamic equilibrium or homeostasis. Until now, the oral delivery of PUFA metabolites or derivatives has not been practical because they are typically oils in their neat state, they have an objectionable taste and mouth feel, they cannot utilize established solid oral delivery vehicles, they are easily oxidized, they are metabolized and/or degraded in the acidic environment of the stomach, they have low oral bioavailability in a neat state due to their low water solubility, and they have short systemic half-lives, and most known delivery vehicles for this kind of chemistry provide only impractically short shelf-lives.

In one embodiment, the current invention is a vehicle system that utilizes an enteric coated softgel, which orally delivers a PUFA derived therapeutic or analog in oil form, protects it from oxidation, protects it from the acidic environment and enzymes of the stomach, increases its bioavailability, and extends its systemic delivery over a longer time period than if it was absorbed directly into the systemic circulation, and obviates first-pass metabolism by the liver, and provides a shelf-life of 1-4 years. Up to 95% of prostaglandins, for instance, are cleared on first pass in the lung, liver and kidney, thereby necessitating continuous infusions (Marc J Ostro, PCT/US1992/003895, WO1992019243 A1, Nov. 12, 1992).

Oral Delivery of Therapeutics

In the delivery of therapeutics, a compound is administered to a patient in a therapeutically effective amount. A compound can be administered alone or as part of a pharmaceutically acceptable composition. In addition, a compound or composition can be administered all at once, multiple times, or delivered substantially uniformly over a period of time. Further, the dose of the compound can be varied over time. A compound can be administered using an immediate release formulation, a controlled release formulation, or combinations thereof. The term "controlled release" includes sustained release, delayed release, and combinations thereof.

A pharmaceutical composition of the invention can be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient that would be administered to a patient or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the human treated and further depending upon the route by which the composition is to be administered. By way of example, the composition can comprise between 0.1% and 100% (w/w) active ingredient. A unit dose of a pharmaceutical composition of the invention will generally comprise from about 2 milligrams to about two grams of the active ingredient, and preferably comprises from about 10 milligrams to about 1.0 gram of the active ingredient.

One aspect of the invention relates to a kit comprising a pharmaceutical composition of the invention and instructional material. Instructional material includes a publication, a recording, a diagram, or any other medium of expression which is used to communicate the usefulness of the pharmaceutical composition of the invention for one of the purposes set forth herein in a human. The instructional material can also, for example, describe an appropriate dose of the pharmaceutical composition of the invention. The instructional material of the kit of the invention can, for example, be affixed to a container which contains a pharmaceutical composition of the invention or be shipped together with a container which contains the pharmaceutical composition. Alternatively, the instructional material can be shipped separately from the container with the intention that the instructional material and the pharmaceutical composition be used cooperatively by the recipient.

The invention also includes a kit comprising a pharmaceutical composition and a delivery device for delivering the composition to a human. By way of example, the delivery device can be a dosage-measuring container for oral delivery, but also may include a squeezable spray bottle, a metered-dose spray bottle, an aerosol spray device, an atomizer, a dry powder delivery device, a self-propelling solvent/powder-dispensing device, a syringe, a needle, or a tampon for administration in different forms. The kit can further comprise an instructional material as described herein. The kit also comprises a container for the separate compositions, such as a divided bottle or a divided foil packet. Additional examples of containers include syringes, boxes, bags, and the like. Typically, a kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

It may be desirable to provide a memory aid on the kit, e.g., in the form of numbers next to the tablets or capsules whereby the numbers correspond with the days of the regimen that the tablets or capsules so specified should be ingested. Another example of such a memory aid is a calendar printed on the card, e.g., as follows "First Week, Monday, Tuesday, . . . etc. . . . Second Week, Monday, Tuesday," etc. Other variations of memory aids will be readily apparent. A "daily dose" can be a single tablet or capsule or several pills or capsules to be taken on a given day.

In another embodiment of the present invention, a dispenser designed to dispense the daily doses one at a time in the order of their intended use is provided. Preferably, the dispenser is equipped with a memory aid, so as to further facilitate compliance with the dosage regimen. An example of such a memory aid is a mechanical counter, which indicates the number of daily doses that have been dispensed. Another example of such a memory aid is a battery-powered micro-chip memory coupled with a liquid crystal readout, or audible reminder signal which, for example, reads out the date that the last daily dose has been taken and/or reminds one when the next dose is to be taken.

Solid dosage forms for oral administration include capsules, tablets, powders, and granules. In such solid dosage forms, the active compound is admixed with at least one inert customary excipient (or carrier) such as sodium citrate or cyclodextrins and derivatives thereof or dicalcium phosphate or (a) fillers or extenders, as for example, starches, lactose, sucrose, mannitol, or silicic acid; (b) binders, as for example, carboxymethylcellulose, alginates, gelatin, polyvinylpyrrolidone, sucrose, or acacia; (c) humectants, as for example, glycerol; (d) disintegrating agents, as for example, agar-agar, calcium carbonate, potato or tapioca starch, alginic acid, certain complex silicates, or sodium carbonate; (e) solution retarders, as for example, paraffin; (f) absorption accelerators, as for example, quaternary ammonium compounds; (g) wetting agents, as for example, cetyl alcohol or glycerol monostearate; (h) adsorbents, as for example, kaolin or bentonite; and/or (i) lubricants, as for example, talc, calcium stearate, magnesium stearate, solid polyethylene glycols, sodium lauryl sulfate, or mixtures thereof. In the case of capsules and tablets, the dosage forms may also comprise buffering agents.

Delivery of lipid therapeutics for oral administration typically takes the form of capsules, which can deliver a PUFA derived therapeutic or analog in oil form. Capsules can be prepared with coatings or shells, such as enteric coatings and others well known in the art. They may also contain opacifying agents, and can also be of such composition that they release the active compound or compounds in a delayed manner. Examples of embedding compositions that can be used are polymeric substances and waxes. The active compounds can also be in micro-encapsulated form, if appropriate, with one or more of the above-mentioned excipients.

Solid compositions of a similar type may also be used as fillers in soft or hard filled gelatin capsules using such excipients as lactose or milk sugar, as well as high molecular weight polyethylene glycols, and the like. Hard capsules comprising the active ingredient can be made using a physiologically degradable composition, such as gelatin. Such hard capsules comprise the active ingredient, and can further comprise additional ingredients including, for example, an inert solid diluent such as calcium carbonate, calcium phosphate, or kaolin. Soft gelatin capsules comprising the active ingredient can be made using a physiologically degradable composition, such as gelatin. Such soft capsules comprise the active ingredient, which can be mixed with water or an oil medium such as peanut oil, coconut oil, liquid paraffin, or olive oil.

Oral compositions can be made, using known technology, which specifically release orally-administered agents in the small or large intestines of a human patient. For example, formulations for delivery to the gastrointestinal system, including the colon, include enteric coated systems, based, e.g., on methacrylate copolymers such as poly(methacrylic acid, methyl methacrylate), which are only soluble at pH 6 and above, so that the polymer only begins to dissolve on entry into the small intestine. The site where such polymer formulations disintegrate is dependent on the rate of intestinal transit and the amount of polymer present. For example, a relatively thick polymer coating is used for delivery to the proximal colon (Hardy et al., Aliment. Pharmacol. Therap. (1987) 1:273-280). Polymers capable of providing site-specific colonic delivery can also be used, wherein the polymer relies on the bacterial flora of the large bowel to provide enzymatic degradation of the polymer coat and hence release of the drug. For example, azopolymers (U.S. Pat. No. 4,663,308), glycosides (Friend et al., J. Med. Chem. (1984) 27:261-268) and a variety of naturally available and modified polysaccharides (see PCT application PCT/GB89/00581) can be used in such formulations.

Pulsed release technology such as that described in U.S. Pat. No. 4,777,049 can also be used to administer the active agent to a specific location within the gastrointestinal tract. Such systems permit drug delivery at a predetermined time and can be used to deliver the active agent, optionally together with other additives that my alter the local microenvironment to promote agent stability and uptake, directly to the colon, without relying on external conditions other than the presence of water to provide in vivo release.

The compounds of the present invention and the pharmaceutically acceptable salts of the same, can be administered to a patient at dosage levels in the range of from about 0.01 to about 1,000 mg per day. For a normal adult human having a body weight of about 70 kg, a dosage in the range of from about 0.01 to about 300 mg is typically sufficient, with 1-10 mg a preferred dosage. However, some variability in the general dosage range may be required depending upon the age and weight of the subject being treated, the intended route of administration, the particular compound being administered and the like. The determination of dosage ranges and optimal dosages for a particular patient is well within the ability of one of ordinary skill in the art having the benefit of the instant disclosure. It is also noted that the compounds of the present invention can be used in sustained release, controlled release, and delayed release formulations, which forms are also well known to one of ordinary skill in the art.

It is not critical whether the compounds of the present invention are administered directly to the cell, to a tissue comprising the cell, a body fluid that contacts the cell, or a body location from which the compound can diffuse or be transported to the cell. It is sufficient that the compound is administered to the patient in an amount and by a route whereby an amount of the compound sufficient to mobilize lipids in the cell arrives, directly or indirectly at the cell. The minimum amount varies with the identity of the compounds.

The specific dosage and dosage range that can be used depends on a number of factors, including the requirements of the patient, the severity of the condition being treated, and the pharmacological activity of the compound being administered. The determination of dosage ranges and optimal dosages for a particular patient is well within the ordinary skill of one in the art in view of this disclosure. It is understood that the ordinarily skilled physician, dentist, or veterinarian will readily determine and prescribe an effective amount of the compound to mobilize lipid stores, induce weight loss, or inhibit appetite in the patient. In so proceeding, the physician or veterinarian can, for example, prescribe a relatively low dose at first, subsequently increasing the dose until an appropriate response is obtained. It is further understood, however, that the specific dose level for any particular human will depend upon a variety of factors including the activity of the specific compound employed, the age, body weight, general health, gender, and diet of the human, the time of administration, the route of administration, the rate of excretion, any drug combination, and the severity of any disorder being treated.

The invention further contemplates formulating combination pharmaceutical compositions which include both a compound as described and an anesthetic agent. Such compositions are useful in medical procedures including, but not limited to, general anesthesia, sedation for mechanically ventilated subjects, and procedural sedation. In general, an "anesthetic agent" is a drug that brings about a state of anesthesia in a subject. However, while many current anesthetic agents produce unconsciousness, they provide no analgesia and must be used in combination with other drugs. For example, propofol is approved in more than fifty countries, and generic versions are available. Propofol is regularly administered in combination with opioids, such as fentanyl, alfentanil, remifentanil and sufentanil, to provide combination hypnotic effect and pain alleviation. As can be appreciated, compounds of the present invention are suitable for replacing such opioid analgesics in combination anesthetic/analgesic formulations and for use in related medical procedures. A variety of anesthetic agents may be used in combination with the present compounds, including intravenous agents such as barbiturates, benzodiazepines, etomidate, ketamine and propofol. In one embodiment, the analgesic compound designated CMX-020 is combined in a pharmaceutical composition with propofol, (available from Astra Zeneca under the tradename DIPRIVAN) to provide an intravenously administered formulation providing both hypnotic and analgesic effects.

The invention further contemplates formulating combination pharmaceutical compositions which include both a therapeutic and a delivery vehicle for delivery of therapeutics. This oral delivery vehicle enables the development of therapeutics because it uniquely provides protection from oxidation, protection from the stomach's acidic environment and metabolic enzymes, avoidance of first-pass metabolism, slow time-release into the systemic circulation, high bioavailability, ability to deliver drug combinations with one or more of the above chemistries with other chemistries, suited to synergistic combinations of molecules such as CMX-020 with other pain therapeutics, tamper-resistant, and 1-4 years shelf-life.

Accordingly, the invention encompasses an oral delivery vehicle with certain compositions of DHA/EPA that have the following ingredients: EPA C20:5 n-3, EPA C20:5 n-3 expressed as TG, DHA C22:6 n-3, DHA C22:6 n-3 expressed as TG, Tocopherol (mixed), Omega-3 acids, Omega-3 acids expressed as TG, Cholesterol, Triglycerides, Partial triglycerides, or combinations of such ingredients.

Delivery of Arachidonic Acid Analogs

Arachidonic acid (AA) analogs have analgesic effects similar to morphine and other opioid analgesics. However, these compounds have a number of different delivery options possible, including brain injections, DRG injections, intraperitoneal injections, intranasal administration, blood injections, transdermal, or oral delivery, that are not possible with conventional pain treatments. Chemical analogs of AA may be engineered or particularly delivered to have a more sustained effect than traditional analgesics. Liposomes, mycelles, cyclodextrins, and emulsifiers can be used in to make AA analog preparations more soluble and easier to administer and/or more stable.

AA and other polyunsaturated fatty acids including eicosapentaenoic acid (EPA) and docosahexaenoic acid (DHA) are catalyzable substrates for cytochrome P450 epoxygenase (CYP4X1) in neurons. AA, for example, is converted to four regioisomers of EETs (i.e., 5,6-EET; 8,9-EET; 11,12-EET and 14,15-EET) by CYP4X1, and application of nanomolar concentrations of EETs (e.g., 11,12-EET) induces suppression of the outward K+ current and inward Na+ current, effectively altering the cellular membrane potential and polarization in neurons. EETs (or other P450 epoxygenase-derived epoxides) and certain selected agonist analogs may therefore regulate neuronal function and contribute to the modulation and treatment of pain.

An exemplary compound of an AA analog may take the following structure:

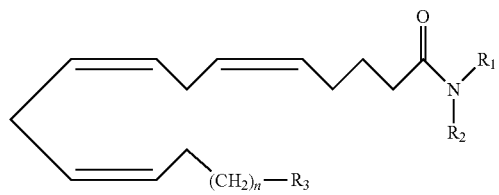

wherein: $R_1$ is H, or a $C_1$-$C_6$ alkyl, $C_2$-$C_6$ alkenyl, $C_3$-$C_6$ cycloalkyl or $C_3$-$C_6$ cycloalkenyl which is unsubstituted or substituted with at least one hydroxyl group; and $R_2$ is H, or a $C_1$-$C_3$ alkyl; $C_3$-$C_6$ cycloalkyl; or $R_1$ and $R_2$ form a $C_3$-$C_6$ heterocyclic ring with the nitrogen bonded to said $R_1$ and $R_2$; wherein any carbon constituent of $R_1$ or $R_2$ can be replaced by O, S, or R'N wherein R' is H or a $C_1$-$C_6$ alkyl;

$R_3$ is

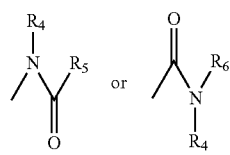

in which:

$R_4$ is H, or a $C_1$-$C_6$ alkyl, $C_2$-$C_6$ alkenyl, $C_3$-$C_6$ cycloalkyl or $C_3$-$C_6$ cycloalkenyl; $R_5$ is a $C_1$-$C_6$ alkyl, $C_3$-$C_6$ cycloalkyl, or $C_1$-$C_6$ alkoxy, or $C_2$-$C_6$ alkyl ether which is unsubstituted or substituted with one or more of hydroxyl, phenyl, phenyloxy, or fluorine, or $R_5$ is $NR_7R_8$, or $C(O)NR_7R_5$ in which $R_7$ and $R_5$ are independently selected from H, a $C_1$-$C_6$ alkyl, $C_2$-$C_6$ alkenyl, $C_3$-$C_6$ cycloalkyl, or $C_3$-$C_6$ cycloalkenyl group; $R_6$ is H, or a $C_1$-$C_6$ alkyl, $C_2$-$C_6$ alkenyl, $C_3$-$C_6$ cycloalkyl, or $C_3$-$C_6$ cycloalkenyl group; wherein any carbon constituent of $R_4$, $R_5$, $R_6$, $R_7$ or $R_8$ can be replaced by O, S, or RN wherein R' is H or a $C_1$-$C_6$ alkyl; and n is 0, 1 or 2; or a pharmaceutically acceptable salt thereof.

Exemplary compounds may include the following structures:

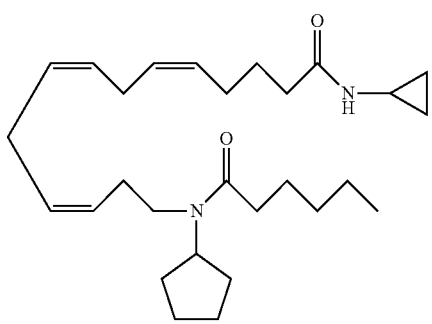

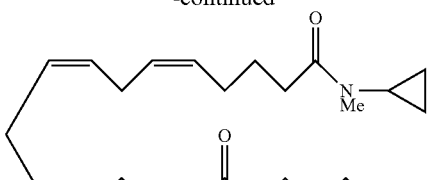

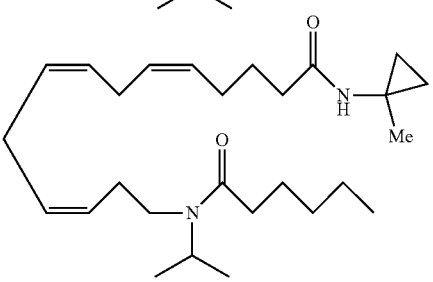

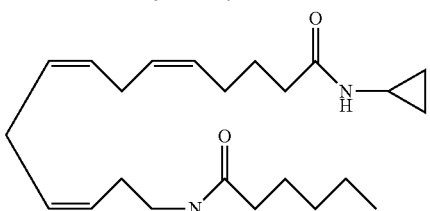

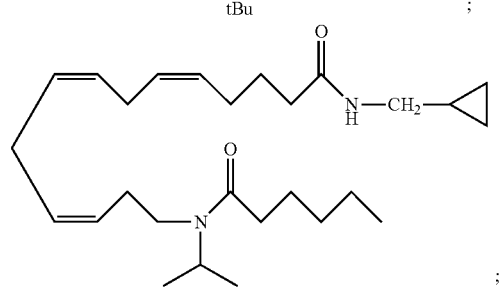

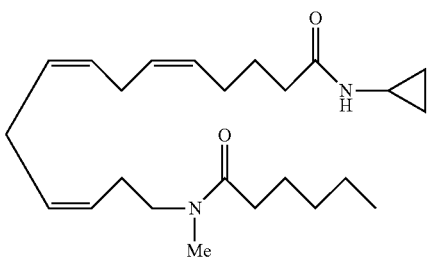

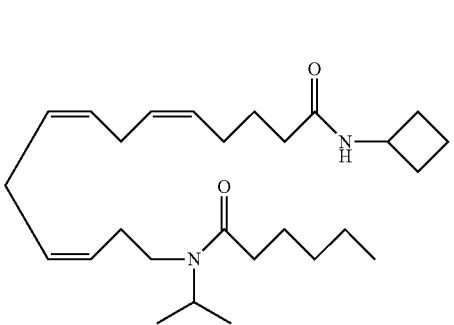

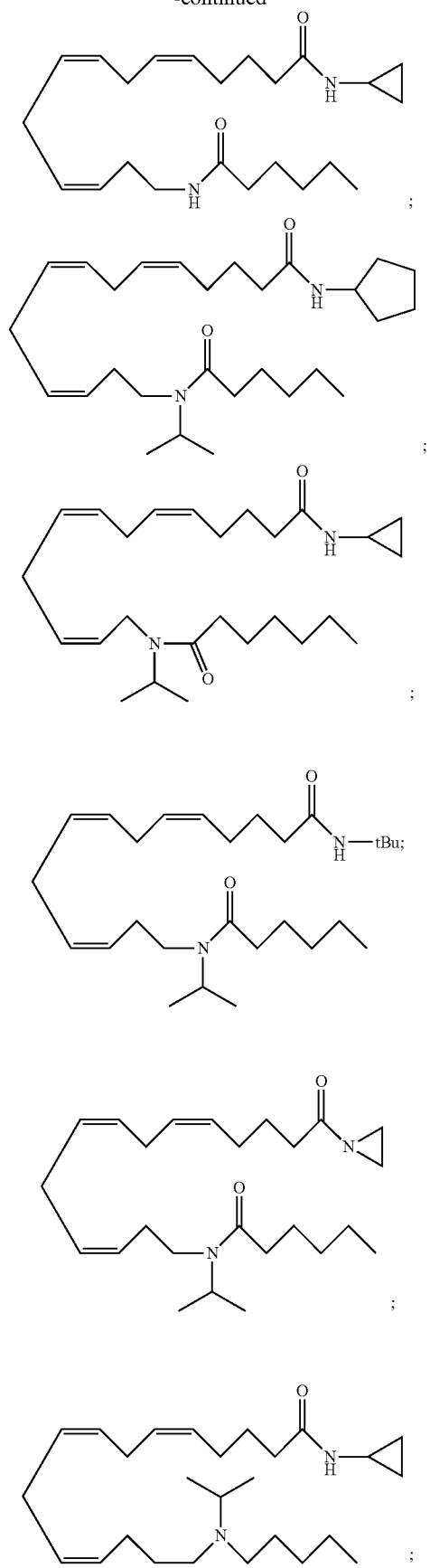
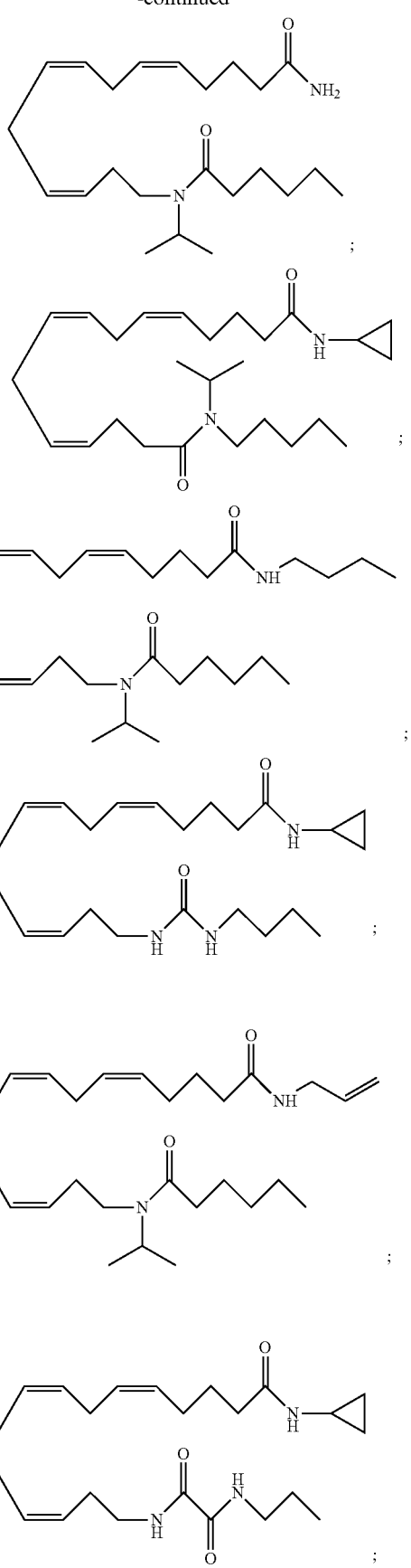

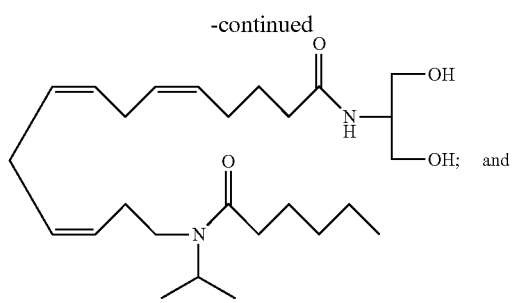

A particular exemplary compound may have the following structure:

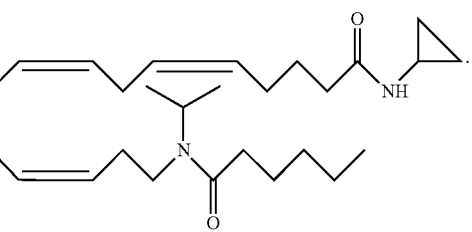

An exemplary compound of an AA analog may also take the following structure:

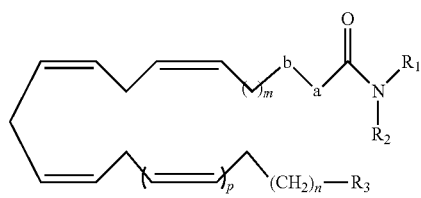

wherein:
R$_1$ is H, or a C$_1$-C$_6$ alkyl, C$_3$-C$_6$ alkenyl, C$_3$-C$_6$ cycloalkyl or C$_3$-C$_6$ cycloalkenyl which is unsubstituted or substituted with a hydroxyl group or a C$_1$-C$_6$ alkyl;

R$_2$ is H, or a C$_1$-C$_3$ alkyl; or R$_1$ and R$_2$ form a C$_3$-C$_6$ heterocyclic ring with the nitrogen bonded to said R$_1$ and R$_2$;

R$_3$ is:

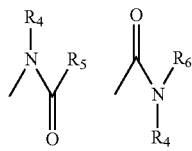

or in which:
R$_4$ is H, or a C$_1$-C$_6$ alkyl, C$_3$-C$_6$ alkenyl, C$_3$-C$_6$ cycloalkyl or C$_3$-C$_6$ cycloalkenyl;

R$_5$ is a C$_1$-C$_6$ alkyl, C$_1$-C$_6$ alkoxy, or C$_2$-C$_6$ alkyl ether which is unsubstituted or substituted with one or more of hydroxyl, phenyl, phenyloxy, or fluorine, or R$_5$ is NR$_7$R$_8$, or C(O)NR$_7$R$_8$ in which R$_7$ and R$_8$ are independently selected from H, a C$_1$-C$_6$ alkyl, C$_3$-C$_6$ alkenyl, C$_3$-C$_6$ cycloalkyl or C$_3$-C$_6$ cycloalkenyl;

R$_6$ is H, or a C$_1$-C$_6$ alkyl, C$_3$-C$_6$ alkenyl, C$_3$-C$_6$ cycloalkyl or C$_3$-C$_6$ cycloalkenyl;

n is 0, 1, 2, 3, or 4;

position a is —CH$_2$—, —CH(CH$_3$)—, —C(CH$_3$)$_2$—, O or NR$_9$ where R$_9$ is H, OH, or a C$_1$-C$_6$ alkyl;

position b is —CH$_2$—, —CH(CH$_3$)—, —C(CH$_3$)$_2$—, O, S, or NR$_{10}$ where R$_{10}$ is H, OH, or a C$_1$-C$_6$ alkyl; wherein position a and b are not both heteroatoms;

m is 0, 1, 2, 3, or 4; wherein when m is 0, then position b is a carbon;

p is 1, 2, or 3; or a pharmaceutically acceptable salt thereof.

A method of synthesizing an exemplary compound may include the steps of:

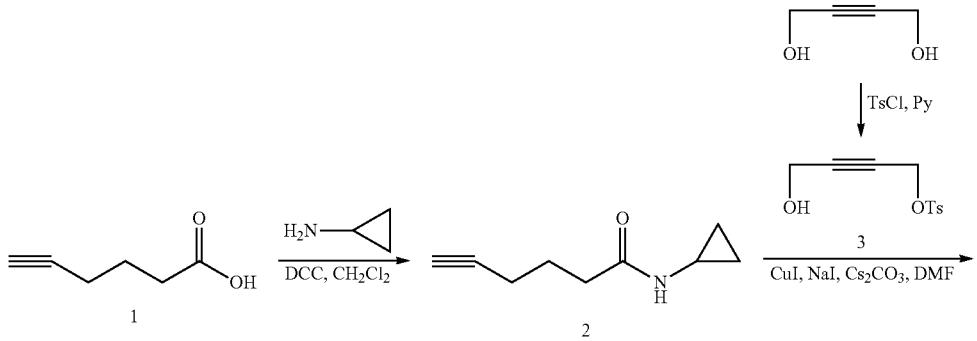

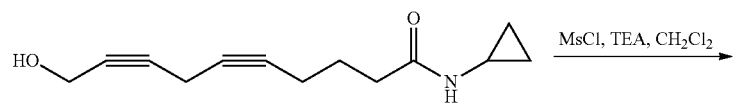

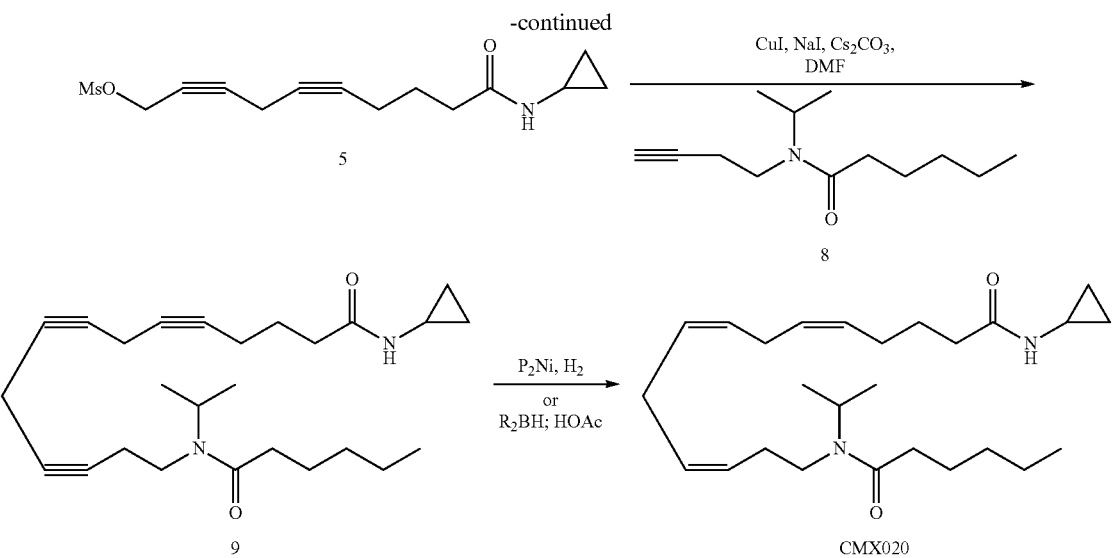

thereby providing a compound.

Another method of providing an exemplary compound includes the steps of:

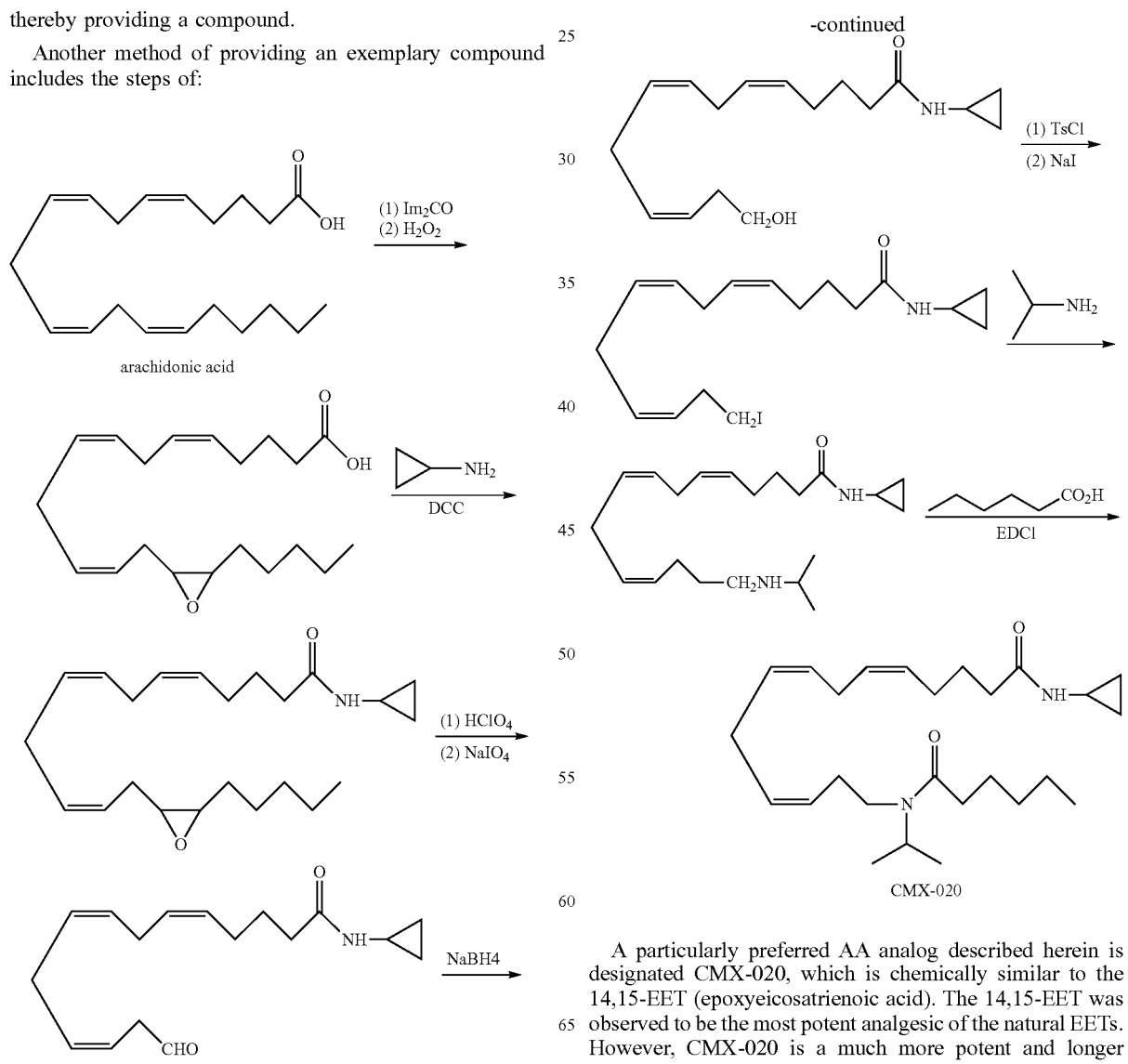

A particularly preferred AA analog described herein is designated CMX-020, which is chemically similar to the 14,15-EET (epoxyeicosatrienoic acid). The 14,15-EET was observed to be the most potent analgesic of the natural EETs. However, CMX-020 is a much more potent and longer lasting analgesic than the natural 14,15-EET. The present invention further encompasses chemical variations based on CMX-020, which are envisioned to be useful in analgesic treatment. The present compounds, including CMX-020, have also demonstrated fever reducing effects and are further envisioned to find use as antipyretic compositions and in fever reducing therapies.

CMX-020 is a first-in-class oral therapeutic compound, derived from the common PUFA arachidonic acid, and enabled through the use of the delivery vehicle of the current invention. CMX-020 is a unique composition of matter (U.S. patent application Ser. No. 13/481,333, which is incorporated herein in its entirety by reference), which provides analgesic efficacy for the treatment of pain. CMX-020 has a multi-modal mechanism of action, similar to the active metabolite of acetaminophen. When CMX-020 is combined with other classes of pain drugs used for chronic pain, such as opioids, pregabalin, gabapentin, tramadol, duloxetine and NSAIDs such as naproxen, the resulting level of efficacy is synergistic—meaning, the resulting efficacy of the combination is significantly higher than it would be when two equivalent doses of a single drug are simply added. Whereas acetaminophen has similar but less potent synergistic qualities, its liver toxicity limits its utilization in chronic pain. CMX-020 is not toxic to the liver unlike acetaminophen, and is therefore more appropriate for use in chronic pain.

Delivery Vehicle Performance of DHA for CMX-020

DHA has shown superior performance as a carrier vehicle for CMX-020, although no one mode of operation is adopted herein in regard to the function of the present invention. The proximal affinity of DHA and CMX-020 and DHA based on similar molecular chemistries likely explains why DHA "carries" CMX-020 so well. DHA is the most abundant fatty acid in the brain as well as the cerebral cortex, skin, sperm, testicles and retina. Despite being such an abundant fatty acid in the brain, DHA cannot be de novo synthesized in brain and must be imported across the blood-brain barrier. While DHA plays critical roles in human physiology, but is minimally synthesized in the body, its mechanisms for transport must be well-developed. In fact, there is a specific mechanism called Mfsd2a that is a major transporter for DHA uptake into brain. Mfsd2a transports long-chain fatty acids, but not with less than a 14-carbon acyl chain. The high bioavailability and slow release profile suggests lymphatic transport likely plays a significant role in moving DHA/CMX-020 into systemic circulation. Lymphatic transport avoids first-pass metabolism and propels lymph slowly through one-way valves prior to emptying in the blood stream at the subclavian veins. Thus, the DHA vehicle increases bioavailability while simultaneously extending the release of CMX-020 into the systemic circulation.

The current delivery vehicle invention is particularly attractive as an enabler for the development of drug combinations of CMX-020 with other drug classes for use in chronic pain indications. The delivery vehicle provides time-release delivery over 4-8 hours, and is also tamper resistant for combining with drugs that have abuse potential. The present invention describes how to enable the co-administration of CMX-020 with opioids, pregabalin, gabapentin, tramadol, duloxetine or NSAIDs such as naproxen for providing increased efficacy, reducing side effects, while delivering within a tamper-resistant delivery vehicle.

Various exemplary embodiments of delivery vehicles (e.g., purified DHA, purified EPA, in both triglyceride and mono-ester forms) according to this invention are now described in the following examples. In these embodiments, specific products identified by Arabic numerals (e.g., 1, 2, 3, etc.) refer to the specific structures so identified in the following description. The following examples are offered for illustrative purposes only and are not intended to limit the scope of the present invention in any way. Indeed, various modifications of the invention in addition to those shown and described herein will become apparent to those skilled in the art from the foregoing description and the following examples and fall within the scope of the appended claims.

III. Examples

Example 1: Comparison of Total Systemic Exposure of CMX-020 with Standard Oily "Bioavailability Enhancers" Vehicles and DHA Triglycerides In FIG. 1, groups of male Sprague-Dawley rats were injected with different delivery vehicles known as bioavailability enhancers for low molecular weight lipophilic compounds. CMX-020, an EET analog, was delivered at equal doses (5 mg/kg) and formulation concentration (2% w/w) into the duodenum. CMX-020 was measured through time in plasma to determine its concentrations. FIG. 1 illustrates that the total systemic exposure of CMX-020 in DHA TG is greater than that of other standard bioavailability enhancing vehicles. Table 1 below displays the absolute bioavailability of CMX-020 via the oral route for all vehicles listed in FIG. 1.

TABLE 1

| Formulation | Class | Absolute Bioavailability |
|---|---|---|
| DHA TG | N/A | 30% |
| Oleic Acid | Omega-9 fatty acid | 8% |
| Miglyol 812N | Medium chain triglyceride (MCT) | 5% |
| Capsulec 62 | Lecithin | 8% |
| Labrasol | Pegylated MCT | 8% |
| Labrafil | Long chain triglycerides (LCT) | 7% |

Example 2: Mixtures of DHA and EPA in Triglyceride Form

Figure 2:
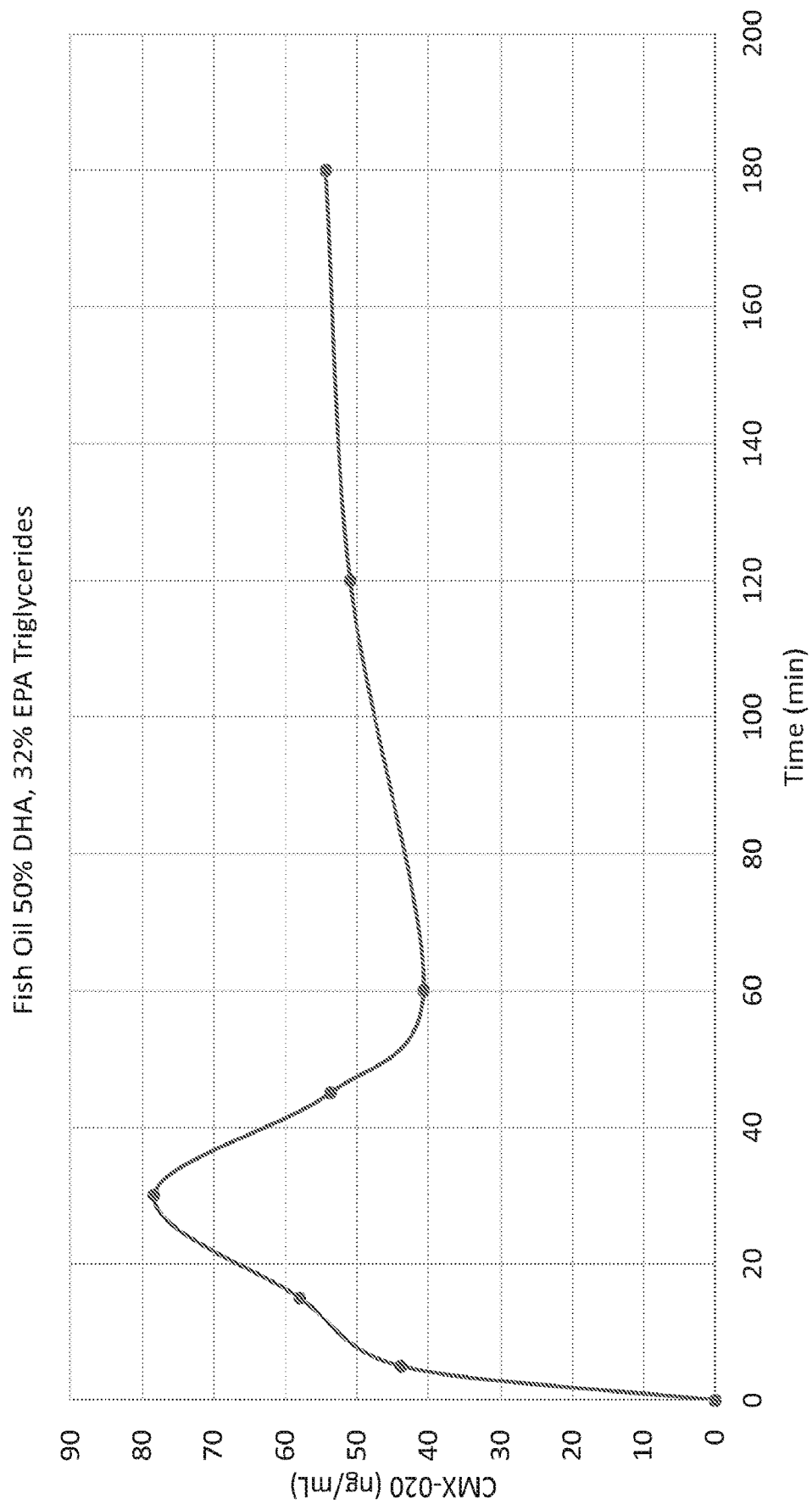
FIG. 2 is a graph showing concentration of CMX-020 measured over time when in a fish oil mixture of DHA and EPA in triglyceride form.

In FIG. 2, groups of male Sprague-Dawley rats were injected with a fish oil mixture of DHA and EPA, 50% and 32%, respectively in triglyceride form derived from cod liver oil. CMX-020, an EET analog, was delivered at 5 mg/kg and formulation concentration (2% w/w) into the duodenum. CMX-020 was measured through time in plasma to determine its concentrations. FIG. 2 illustrates that the systemic exposure of CMX-020 in this vehicle out to 3 hrs shows the compound reaching a steady state, with an associated absolute bioavailability of 16%.

Example 3: Comparison of Purified DHA and EPA Triglycerides

Figure 3:
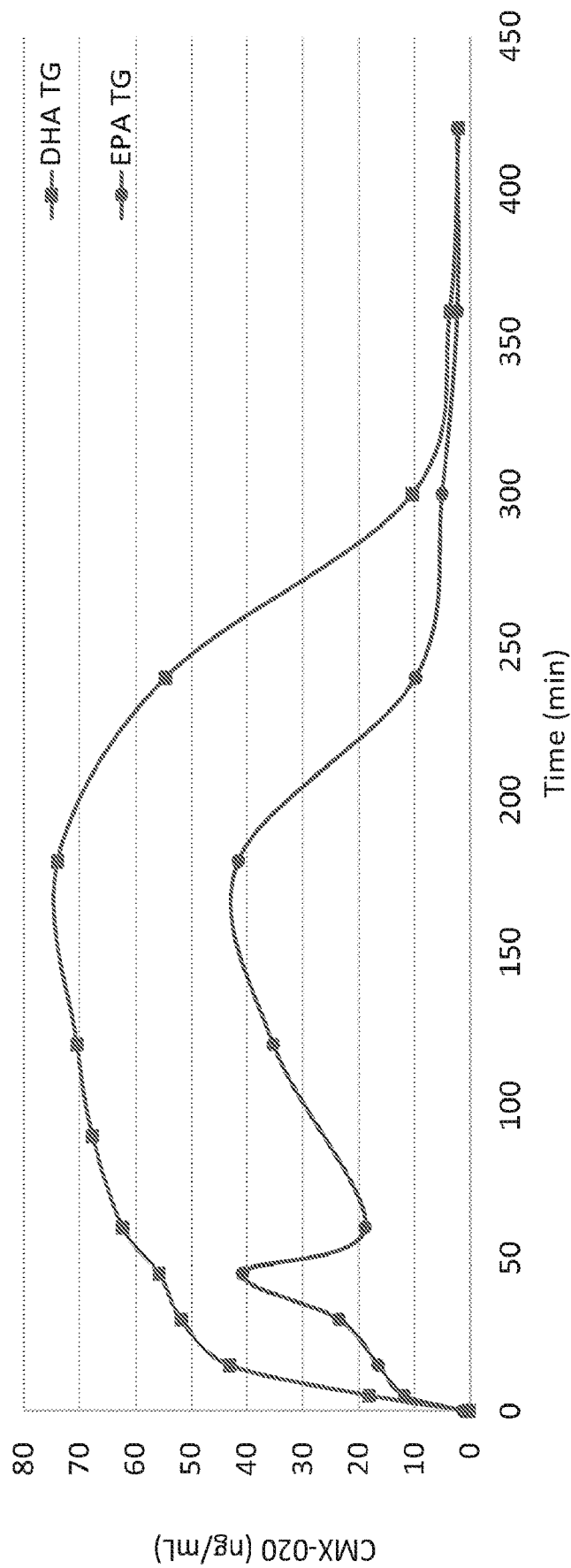
FIG. 3 is a graph showing concentration of CMX-020 measured over time for highly purified DHA and EPA in triglyceride form.

Groups of male Sprague-Dawley rats were injected with CMX-020 using either highly purified DHA or EPA in triglyceride form into the duodenum. FIG. 3 and Table 2 below illustrates that the increased bioavailability is attributed to high levels of DHA rather than high levels of EPA for CMX-020.

TABLE 2

| Formulation | Absolute Bioavailability |
| --- | --- |
| DHA TG | 30% |
| EPA TG | 13% |

Example 4: Ethyl Esters of DHA and EPA

Figure 4:
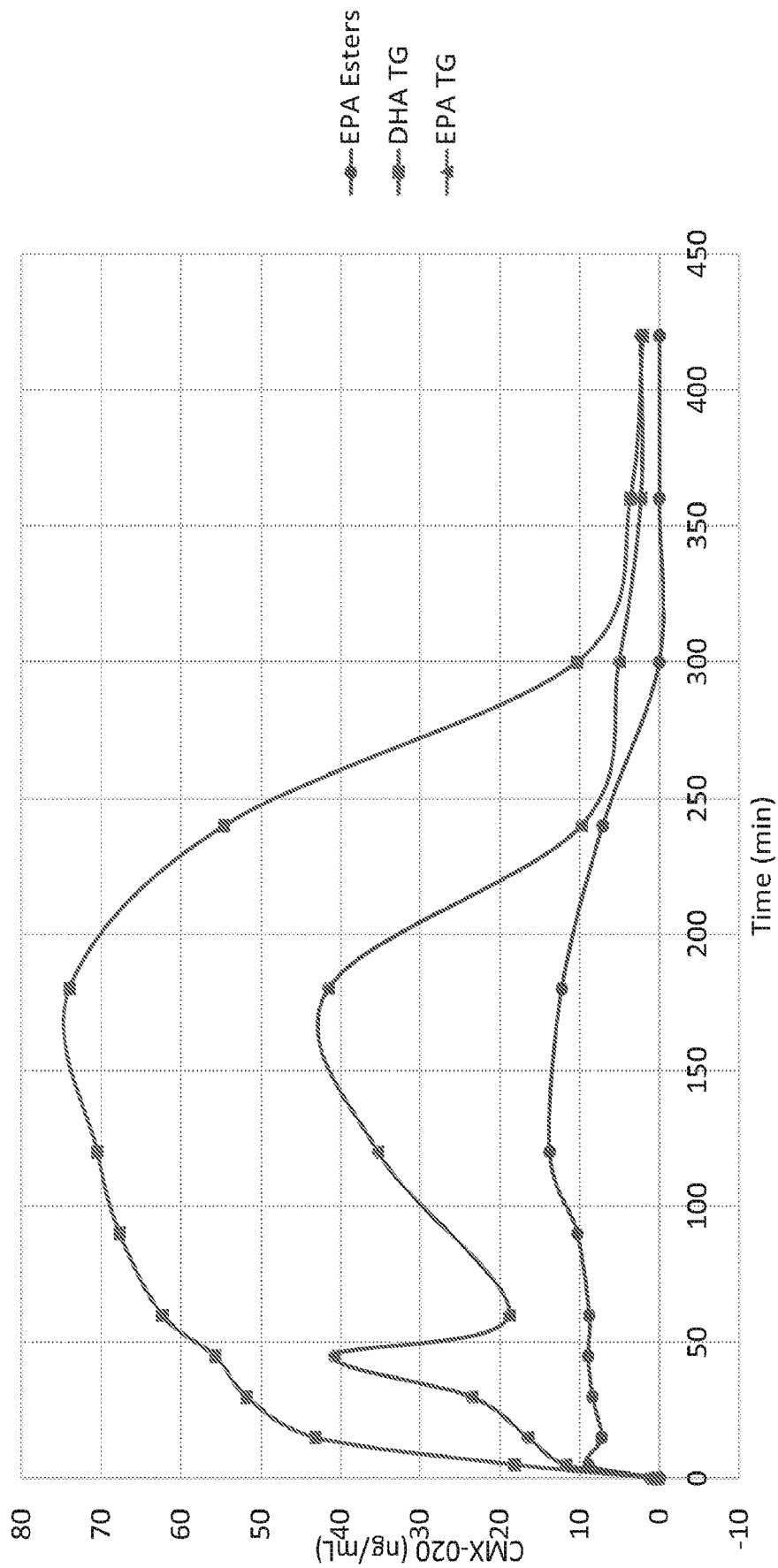
FIG. 4 is a graph showing concentration of CMX-020 measured over time for high purity DHA or EPA in triglyceride or ethyl ester form.

In FIG. 4, groups of male Sprague-Dawley rats were injected with either high purity DHA or EPA in triglyceride or ethyl ester form. CMX-020 was delivered at 5 mg/kg and formulation concentration (2% w/w) into the duodenum. CMX-020 was measured through time in plasma to determine its concentrations. FIG. 4 and Table 3 illustrates that the systemic exposure of CMX-020 in DHA or EPA in triglyceride form is superior to ethyl ester forms of DHA or EPA, in bioavailability.

TABLE 3

| Formulation | Absolute Bioavailability |
| --- | --- |
| DHA TG | 30% |
| EPA TG | 13% |
| EPA Ethyl Ester | 5% |

Figure 5:
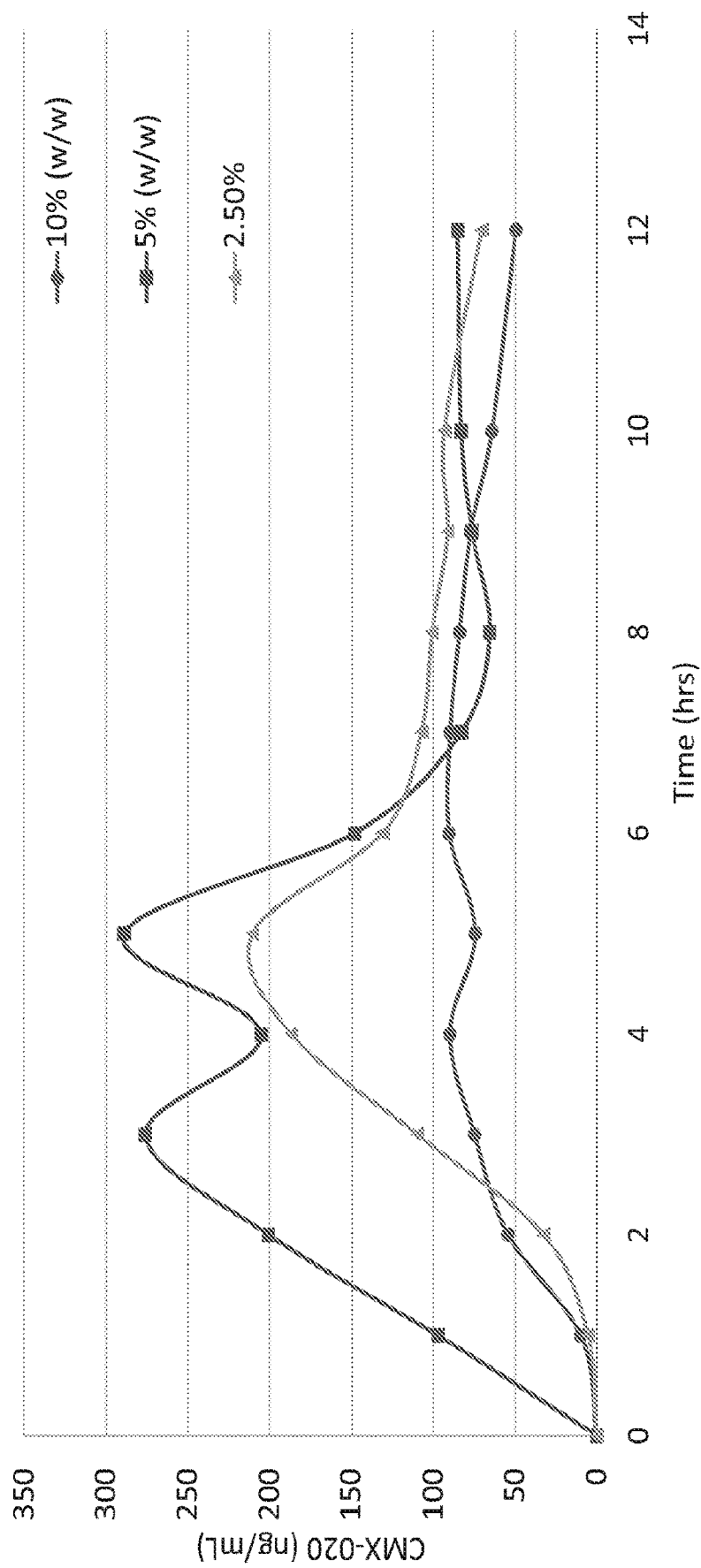
FIG. 5 is a graph showing concentration of CMX-020 measured over time for various concentrations of DHA in triglyceride form.

Example 5: CMX-020 in Different Concentrations Provides Effective Systemic Exposure in Monkey In FIG. 5, groups of male cynomolgus monkey were administered CMX-020 (40 mg total dose) in enterically coated softgels at 10, 5 and 2.5% (w/w) using high purity DHA in triglyceride form as the delivery vehicle. CMX-020 was measured through time in plasma to determine its concentrations. FIG. 5 illustrates that the systemic exposure of CMX-020 in DHA TG at various concentrations provides suitable systemic exposure for more than 12 hours. In this study, the optimal concentration was 5% displaying an absolute bioavailability of 20%.

Figure 6A:
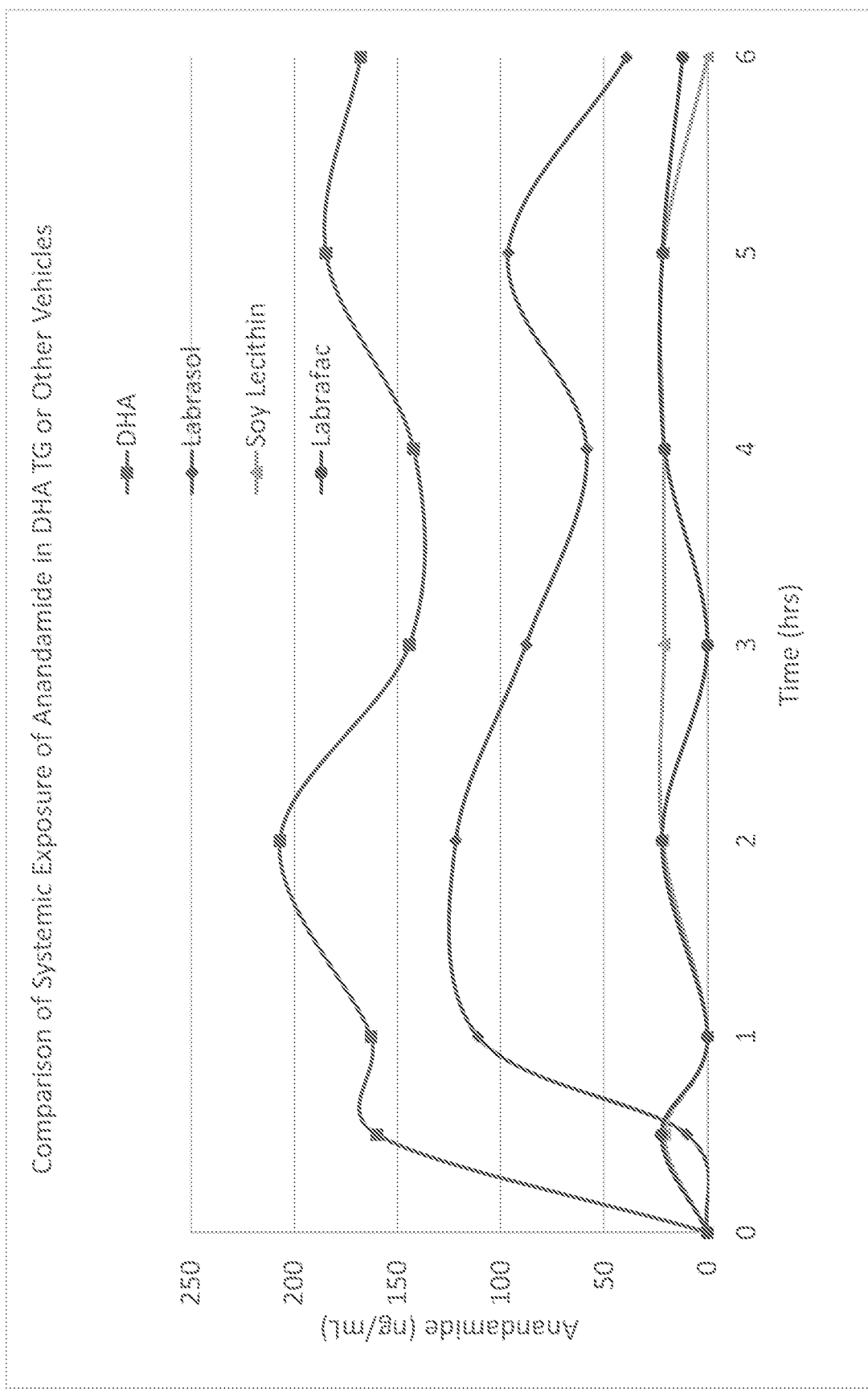
FIG. 6A is a graph showing concentration of Anandamide measured over time when using DHA, Labrasol, Labrafac and soy lecithin as the delivery vehicle.
Figure 6B:
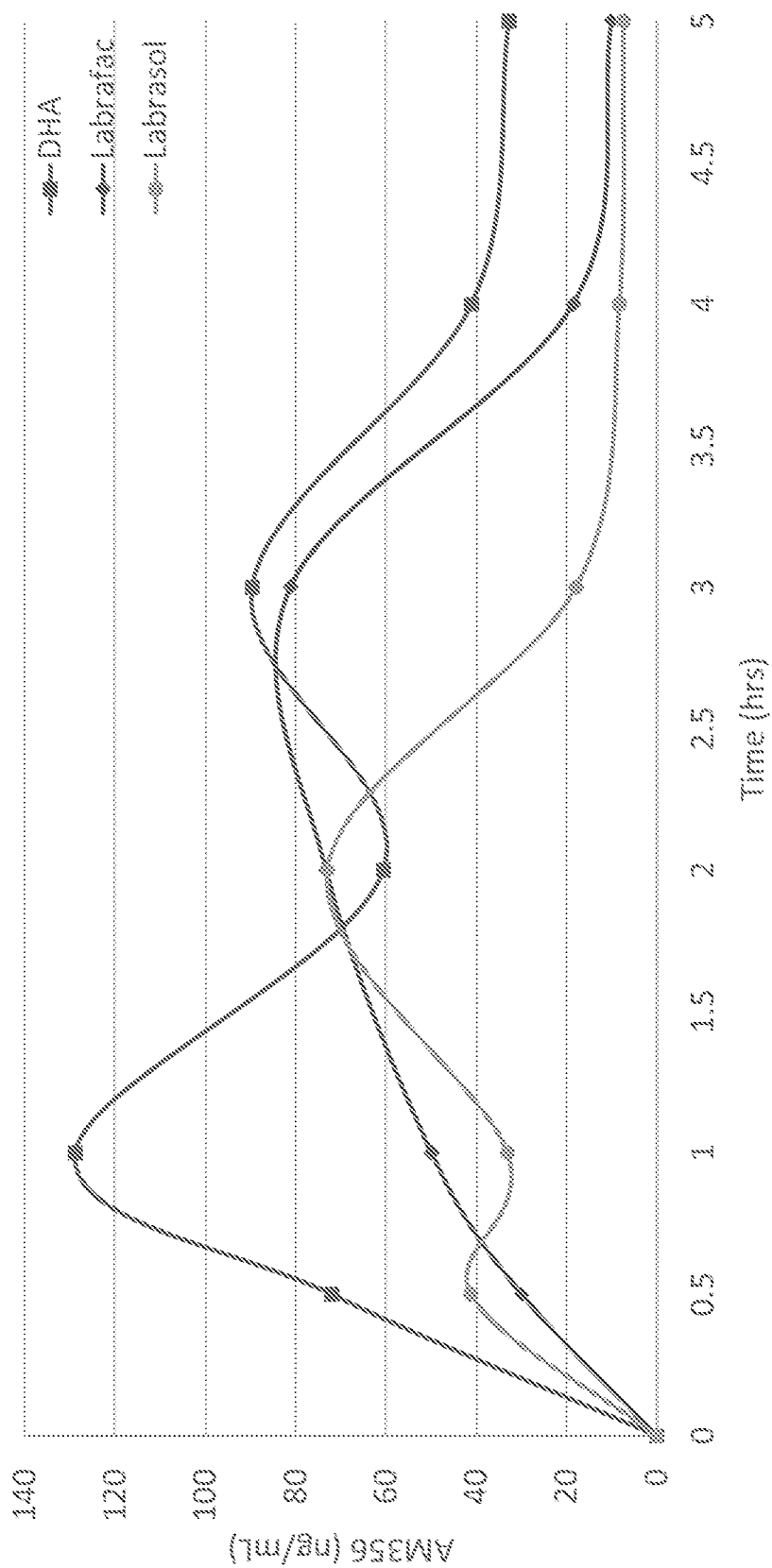
FIG. 6B is a graph showing concentration of AM356 measured over time when using DHA, Labrasol and Labrafac as the delivery vehicle.

Example 6: Arachidonic Acid Derivatives, or Synthetic Analogs of AAS, Also Display Similar Systemic Absorption Profiles to CMX-020 in DHA TG. The Data Below Show Systemic Exposure of Select Analogs Using DHA TG In FIGS. 6A and 6B, groups of male Sprague-Dawley rats were injected with either high purity DHA triglycerides or other standard excipient formulations for the endogenous endocannabinoid anandamide or AM356 (R1 Meth-anandamide). Anandamide was delivered as a 2% solution at 20 mg/kg and AM356 was delivered in a 5% solution at 50 mg/kg into the duodenum. Both analytes were measured through time in plasma to determine its concentrations. FIG. 6A and Table 4 below illustrates that the systemic exposure of Anandamide in either DHA, Labrasol, Labrafac or soy lecithin. DHA in triglyceride form is superior to the other excipients tested, in terms of area under the concentration curve $T_0$ to $T_{last}$. FIG. 6B and Table 5 below illustrates that the systemic exposure of AM356 in either DHA, Labrasol or Labrafac. DHA in triglyceride form is superior to the other excipients tested for both analogs of interest, in terms of area under the concentration curve $T_0$ to $T_{last}$.

TABLE 4

| Formulation | $AUC_{0-t}$ (ng * hr/mL) |
| --- | --- |
| DHA TG | 963.9 |
| Labrasol | 472.5 |
| Labrafac | 81.9 |
| Soy Lecithin | 96 |

TABLE 5

| Formulation | $AUC_{0-t}$ (ng * hr/mL) |
| --- | --- |
| DHA TG | 340.8 |
| Labrafac | 230.4 |
| Labrasol | 148.4 |

Example 7: Arachidonic Acid Derivatives, or Synthetic Analogs of AAs Delivered Orally Using DHA TG, Achieve Greater Systemic Concentrations Versus Other Oily Vehicles In summary, orally administered 20 carbon lipid analogs of arachidonic acid and compounds with arachidonic acid backbones in a vehicle of DHA TG have been shown to outperform standard bioavailability enhancing oily vehicles. As shown in examples 1-6 CMX-020, anandamide and AM356 (structures provided below) reach greater peak plasma concentrations and greater extended time profiles as compared to comparator vehicles on an equivalent mg/kg and concentration basis.

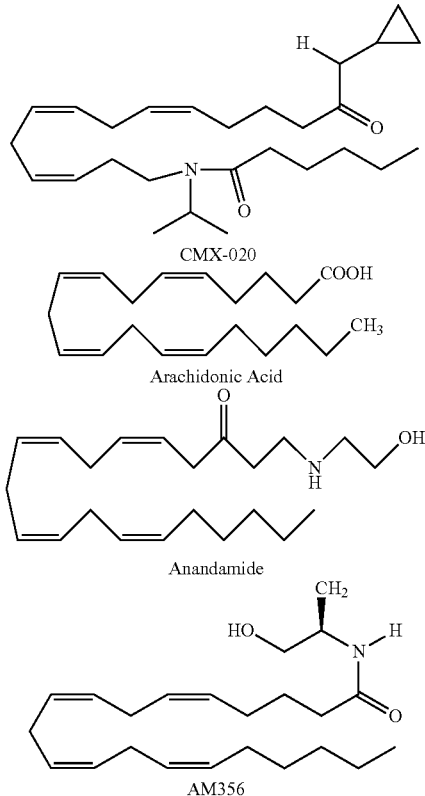

Figure 7:
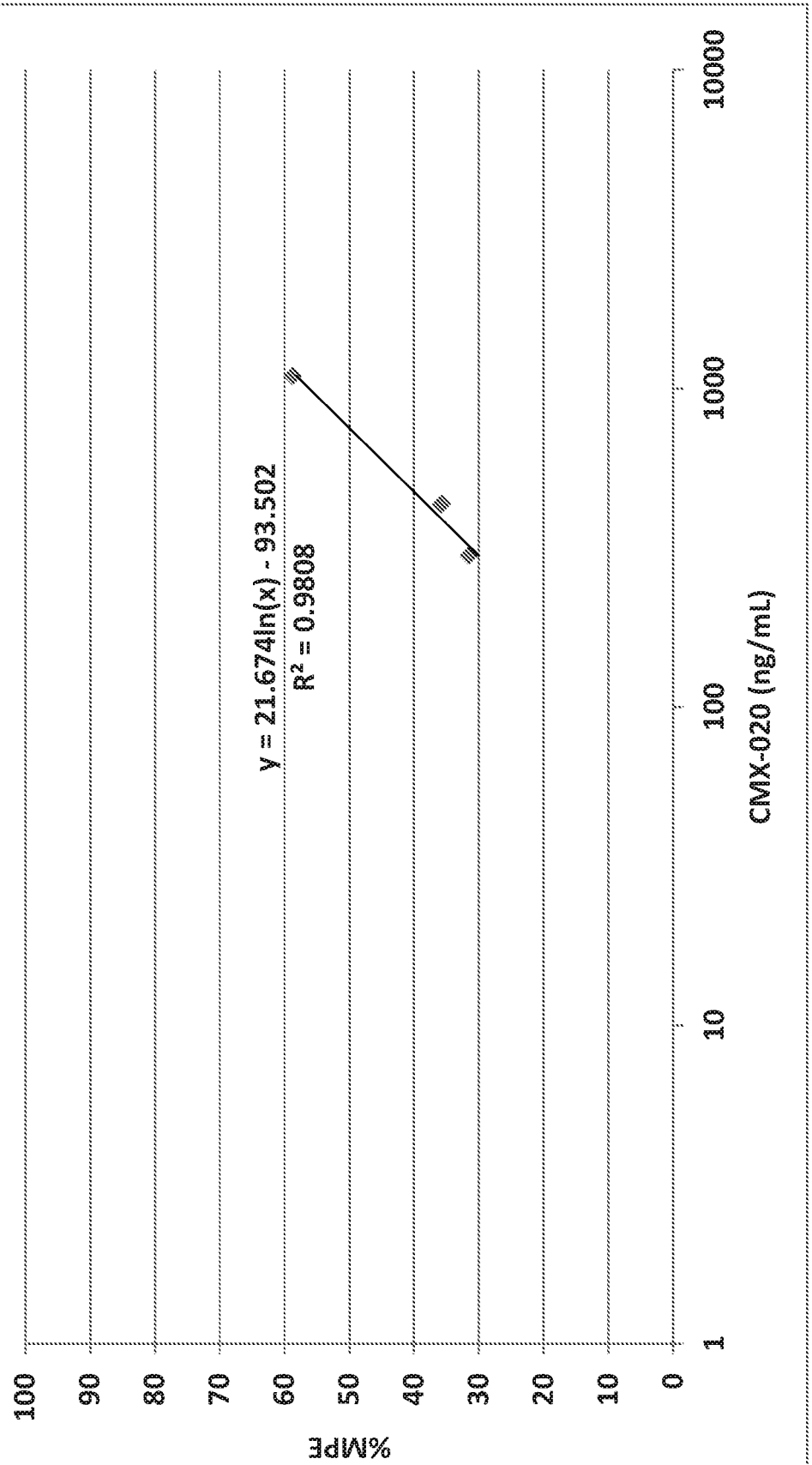
FIG. 7 is a graph showing the analgesic effect of CMX-020 (% MPE=post drug threshold−baseline threshold/cutoff threshold−baseline threshold×100) using high purity DHA in triglyceride form as the delivery vehicle.

Example 8: Arachidonic Acid Derivatives, or Synthetic Analogs of AAs Delivered Using DHA TG, Display Therapeutic Effects. CMX-020 in DHA TG Delivered Orally as an Analgesic. The Data Below Shows Analgesic Effects of CMX-020 Delivered Using DHA TG in Rats Using a Post-Operative Pain Model In FIG. 7, groups of male Sprague Dawley rats were administered CMX-020 intraduodenally at various doses using high purity DHA in triglyceride form as the delivery vehicle. CMX-020 was measured in plasma to determine its concentrations immediately after the efficacy endpoint. Prior to administration, the rat's hindpaw was surgically incised and sutured. 3 hours post-surgery the rats were subjected to mechanical allodynia (Von Frey filament) assessment to quantify the analgesic effect of CMX-020 (% MPE=post drug threshold–baseline threshold/cutoff threshold–baseline threshold×100). FIG. 7 illustrates that the systemic exposure of CMX-020 in DHA TG positively correlates to the efficacy of CMX-020.

Figure 8:
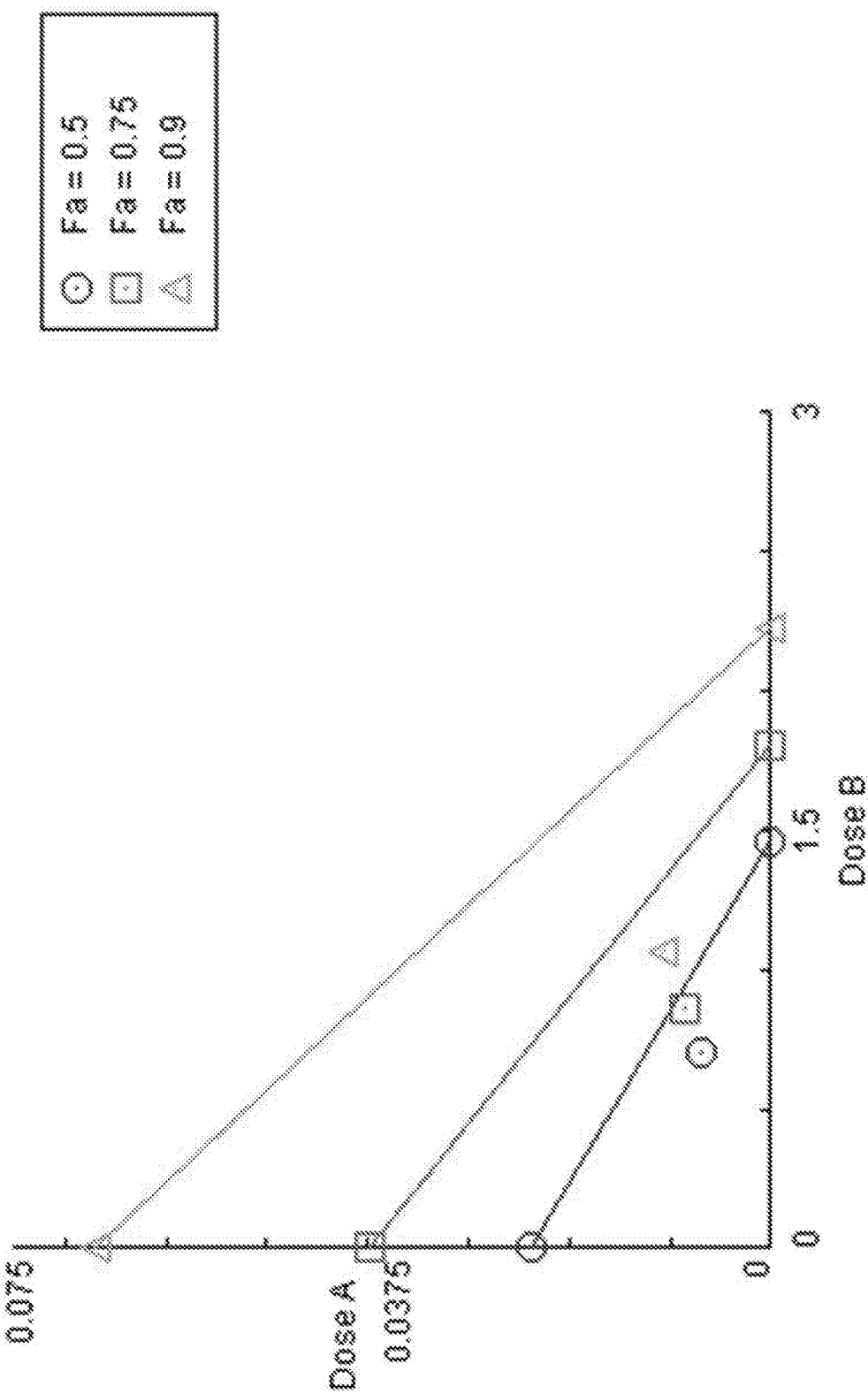
FIG. 8 is a classical isobologram plot for three combinational doses of CMX-020 and Remifentanil in an acute pain tail flick assay.
Figure 9:
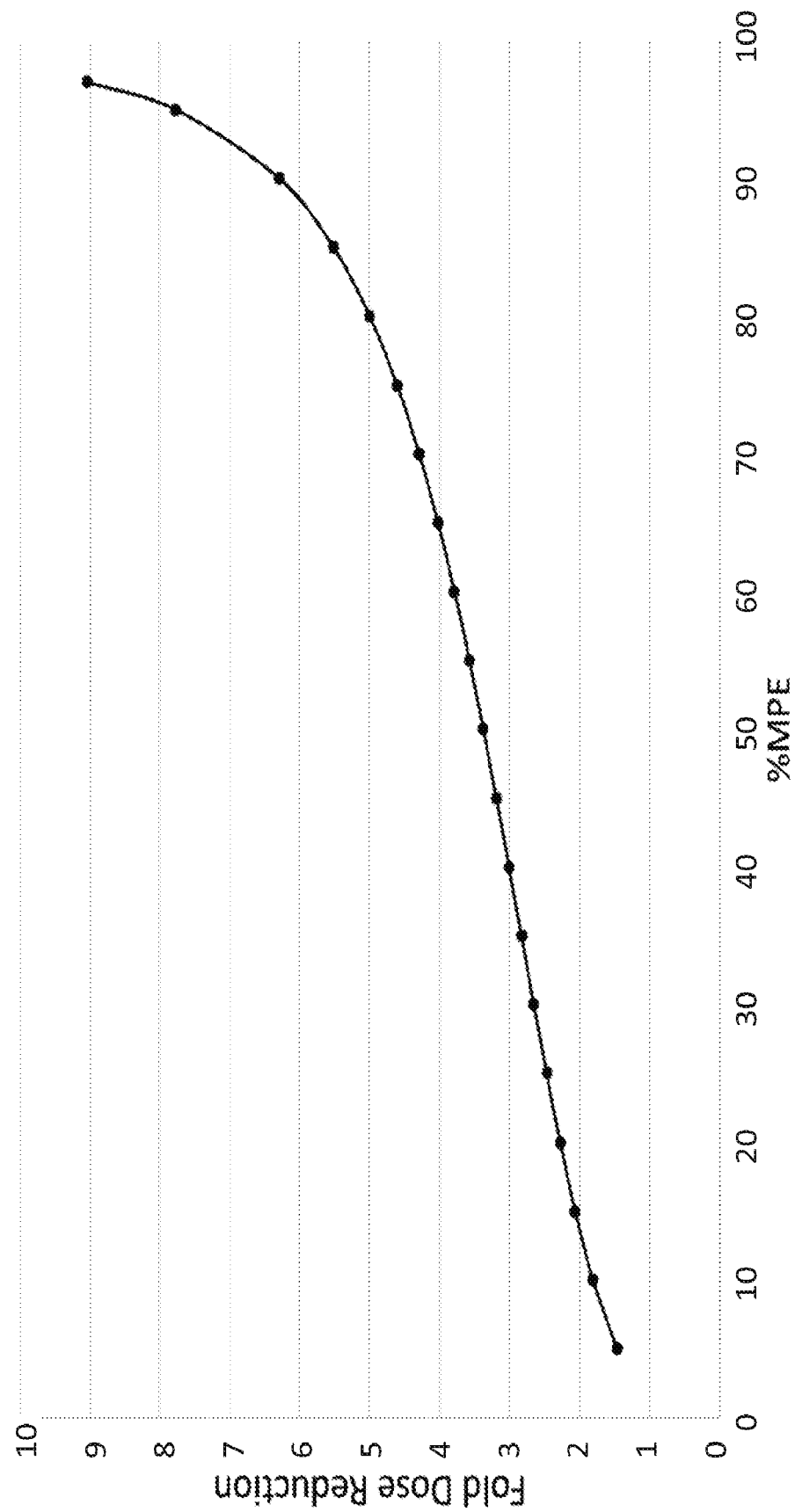
FIG. 9 is a graph showing fold dose reduction of the Remifentanil dose as a function of analgesic effect of CMX-020 (% MPE) in the acute pain tail flick assay.

Example 9: Co-Administration of CMX-020 and Remifentanil Produces a Synergistic Analgesic Effect in the Acute Pain Tail Flick Assay In FIGS. 8 and 9, groups of male Sprague Dawley rats were administered CMX-020 and Remifentanil intravenously over 10 minutes either alone or co-administered at various combinational doses to produce individual dose responses and a combinational dose response. Efficacy was measured using the tail flick assay. The method of Chou-Talalay and CompuSyn computer software were used to automate analysis of dose effect data for each individual drug and their combination. Using a classical isobologram plot (FIG. 8), for three particular dose effect levels, 50%, 75% and 90% inhibition of tail flick response, shows that the analgesic effect of the combinational therapy is greater than a simple additive effect, i.e., below the "line of additivity" (Dose A=Remifentanil, DoseB=CMX-020). The fold reduction of the Remifentanil dose in combination with CMX-020 is greater than 2-fold in efficacy ranges at and greater than 20% (FIG. 9).

Figure 10:
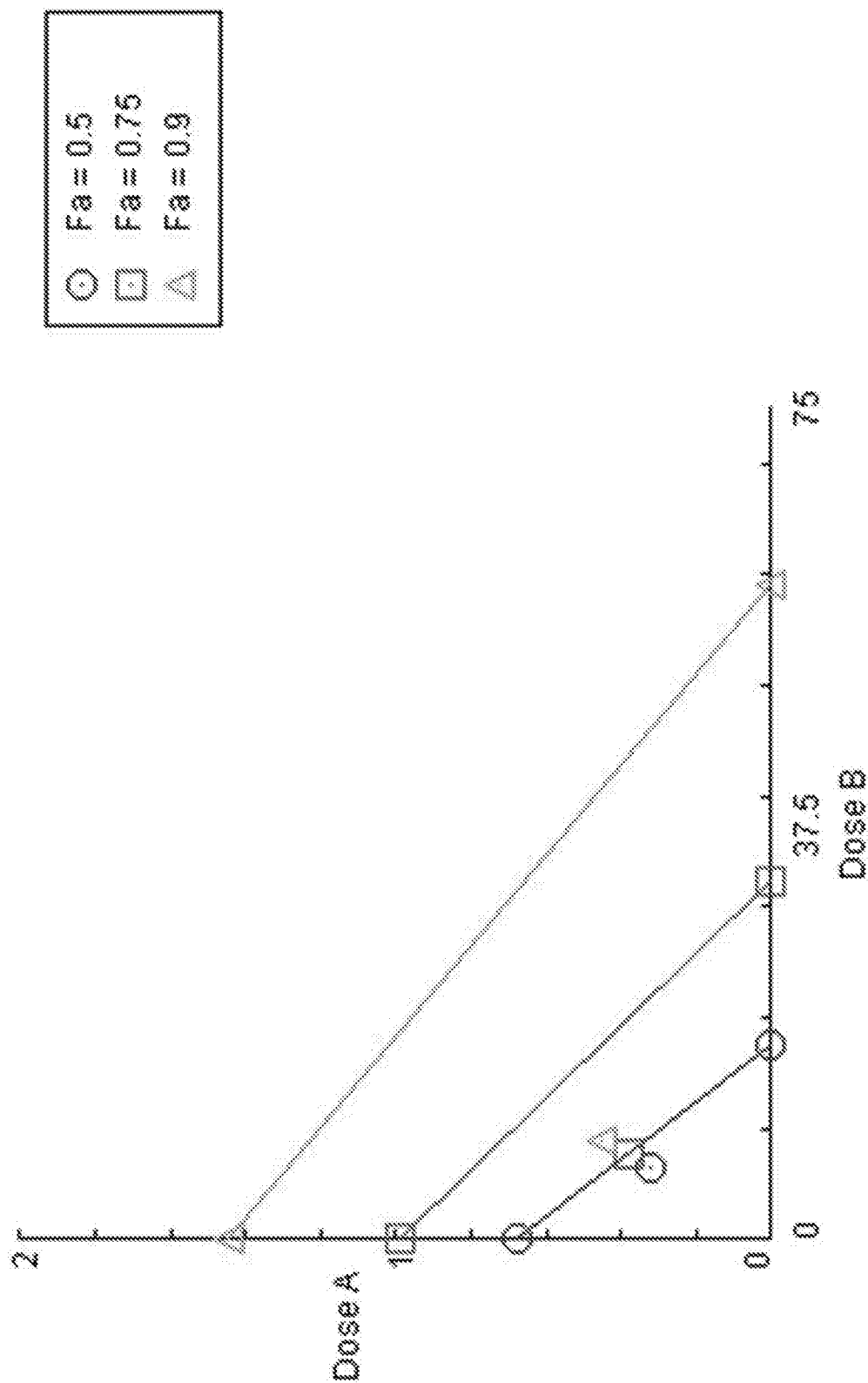
FIG. 10 is a classical isobologram plot for three combinational doses of CMX-020 and Pregabalin in a rodent model of fibromyalgia.
Figure 11:
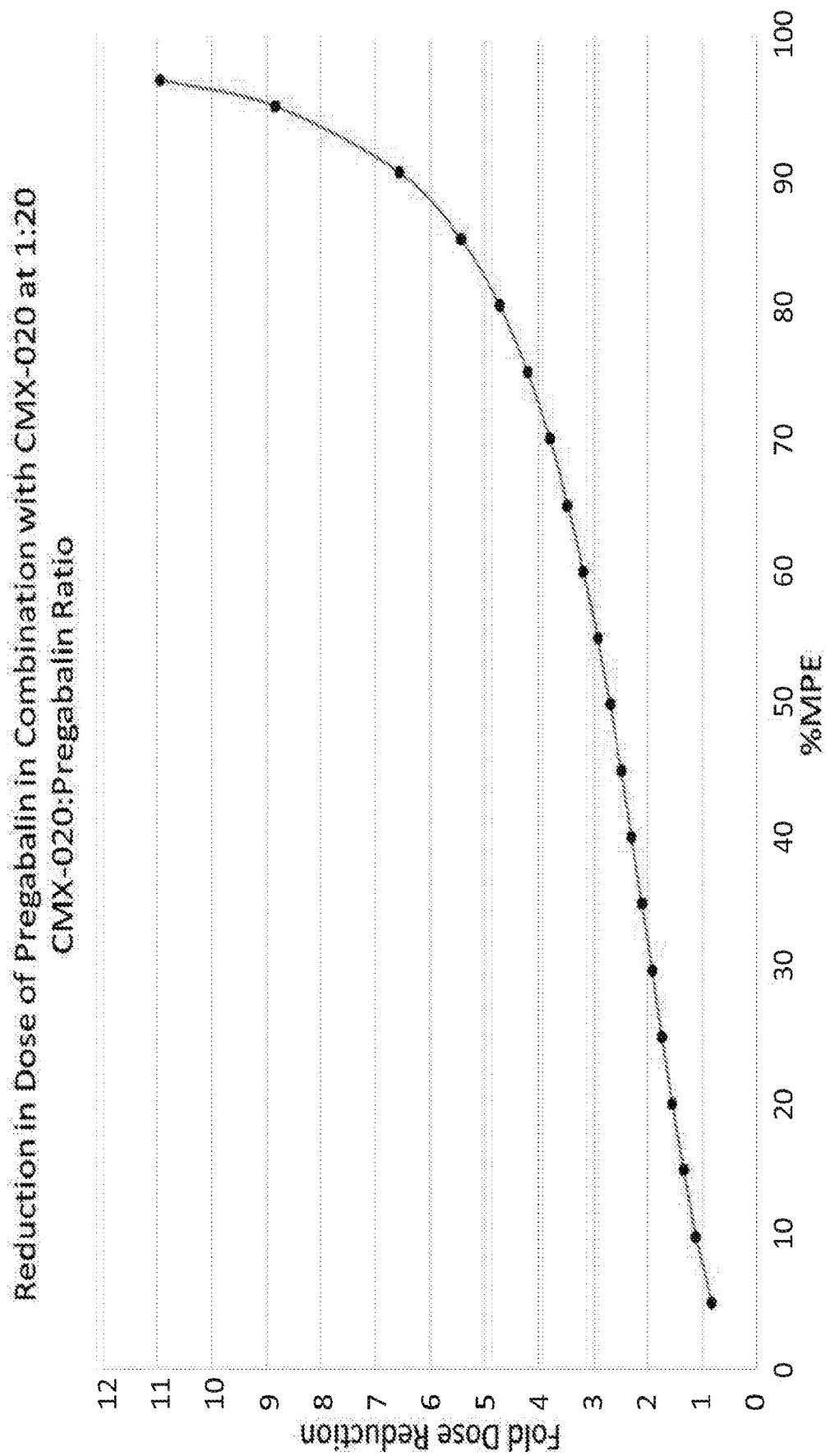
FIG. 11 is a graph showing fold dose reduction of the Pregabalin dose as a function of analgesic effect of CMX-020 (% MPE) in a rodent model of fibromyalgia.

Example 10: Co-Administration of CMX-020 and Pregabalin Produces a Synergistic Analgesic Effect in a Rodent Model of Fibromyalgia In FIGS. 10 and 11, groups of male Sprague Dawley rats were administered daily consecutive reserpine injections (3 days) to induce a rodent model of fibromyalgia. CMX-020 and Pregabalin were administered either alone or co-administered at various combinational doses and efficacy was tested using mechanical allodynia pain thresholds (Von Frey Filaments, up-down method). The method of Chou-Talalay and CompuSyn computer software were used to automate analysis of dose effect data for each individual drug and their combination. Using a classical isobologram plot (FIG. 10), it shows that the analgesic effect of the combinational therapy is greater than a simple additive effect i.e., below the "line of additivity" (Dose A=CMX-020, Dose B=Pregabalin). The fold reduction of Pregabalin in combination with CMX-020 is greater than 2-fold in efficacy ranges at and greater than 35% (FIG. 11).

Figure 12:
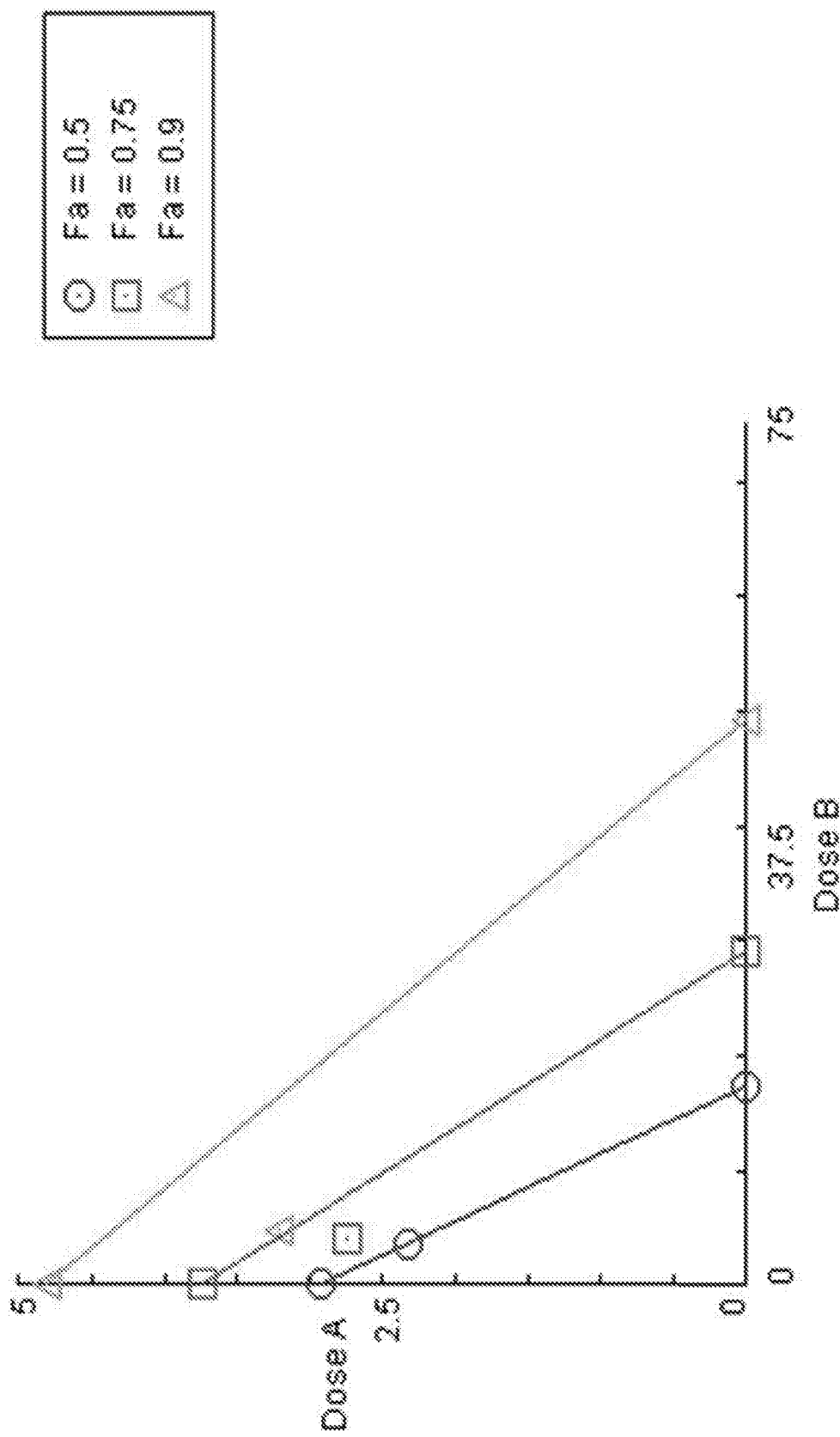
FIG. 12 is a classical isobologram plot for three combinational doses of CMX-020 and Tramadol in a rodent model of osteoarthritis.
Figure 13:
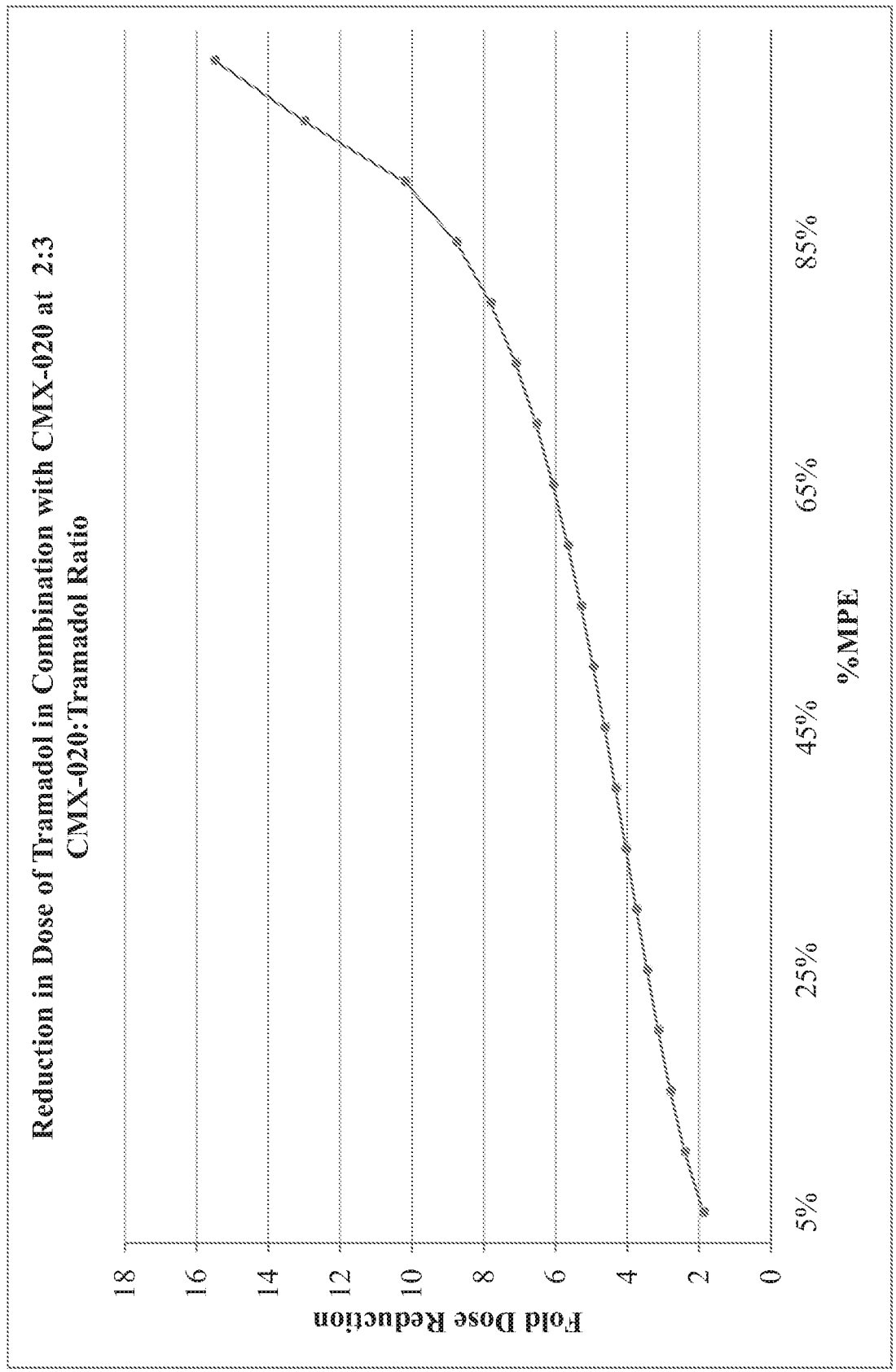
FIG. 13 is a graph showing fold dose reduction of the Tramadol dose as a function of analgesic effect of CMX-020 (% MPE) in a rodent model of osteoarthritis.

Example 11: Co-Administration of CMX-020 and Tramadol Produces a Synergistic Analgesic Effect in a Rodent Model of Osteoarthritis In FIGS. 12 and 13, groups of male Sprague Dawley rats were administered monosodium iodoacetate (MIA) into the knee as a single intra-articular injection resulting in an a late phase (14-28 days) pain response. 2 weeks later treatment with CMX-020 and Tramadol were administered either alone or in combination at various combinational doses and efficacy was tested using mechanical allodynia pain thresholds (Von Frey Filaments, up-down method). The method of Chou-Talalay and CompuSyn computer software were used to automate analysis of dose effect data for each individual drug and their combination. Using a classical isobologram plot (FIG. 12), it shows that the analgesic effect of the combinational therapy is greater than a simple additive effect i.e., below the "line of additivity" (Dose A=CMX-020, Dose B=Tramadol). The fold reduction of Tramadol in combination with CMX-020 is greater than 2-fold in efficacy ranges at and greater than 10% (FIG. 13).

Figure 14:
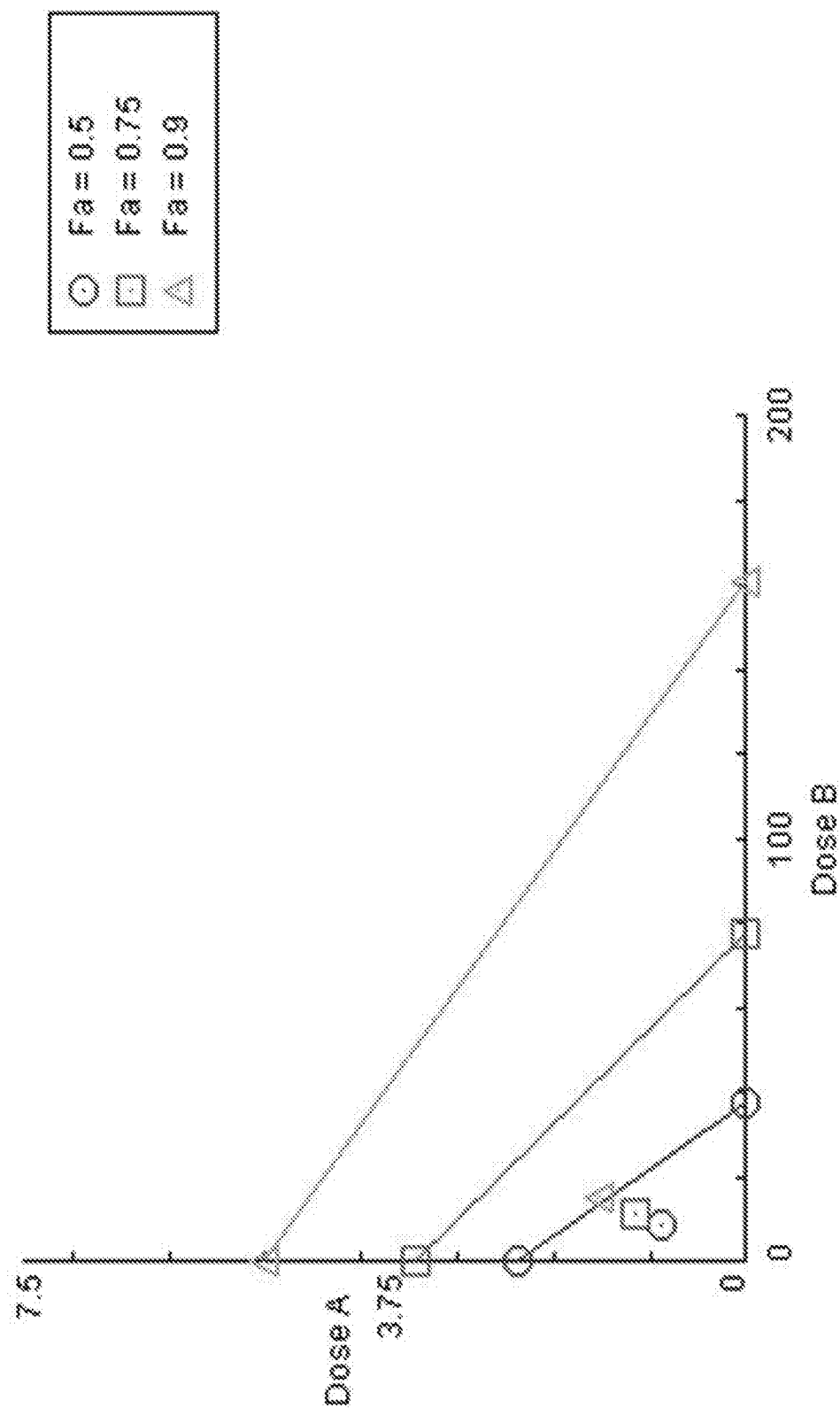
FIG. 14 is a classical isobologram plot for three combinational doses of CMX-020 and Duloxetine in a rodent model of spinal nerve ligation.
Figure 15:
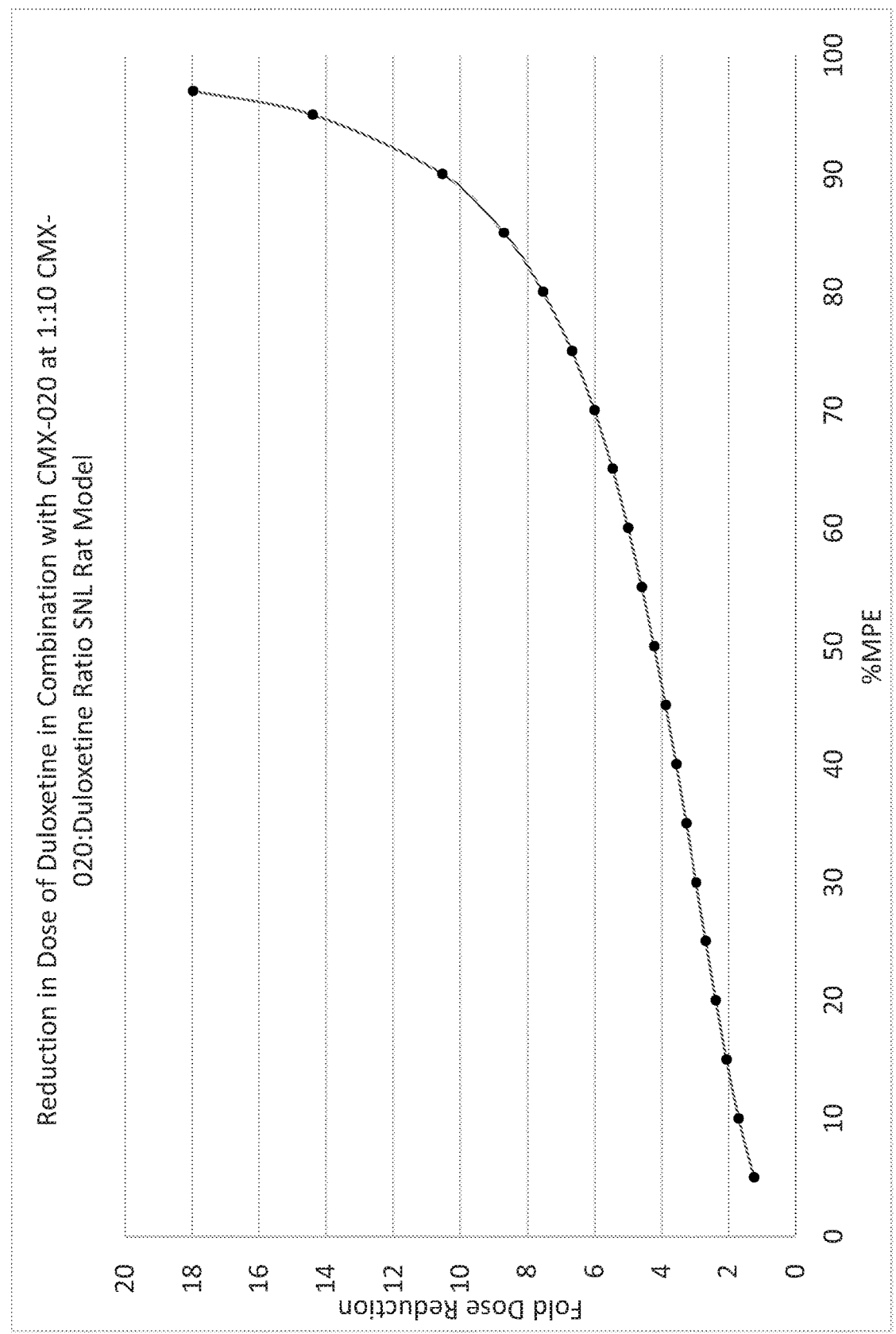
FIG. 15 is a graph showing fold dose reduction of the Duloxetine dose as a function of analgesic effect of CMX-020 (% MPE) in a rodent model of spinal nerve ligation.

Example 12: Co-Administration of CMX-020 and Duloxetine Produces a Synergistic Analgesic Effect in a Rodent Model Spinal Nerve Ligation In FIGS. 14 and 15, groups of male Sprague Dawley rats underwent a spinal nerve ligation method of the left L5 and L6 spinal nerves, inducing a model of peripheral neuropathic pain. 1 weeks later treatment with CMX-020 and Duloxetine were administered either alone or in combination at various combinational doses and efficacy was tested using mechanical allodynia pain thresholds (Von Frey Filaments, up-down method). The method of Chou-Talalay and CompuSyn computer software were used to automate analysis of dose effect data for each individual drug and their combination. Using a classical isobologram plot (FIG. 14), it shows that the analgesic effect of the combinational therapy is greater than a simple additive effect i.e., below the "line of additivity" (Dose A=CMX-020, Dose B=Duloxetine). The fold reduction of Duloxetine in combination with CMX-020 is greater than 2-fold in efficacy ranges at and greater than 20% (FIG. 15).

Figure 16:
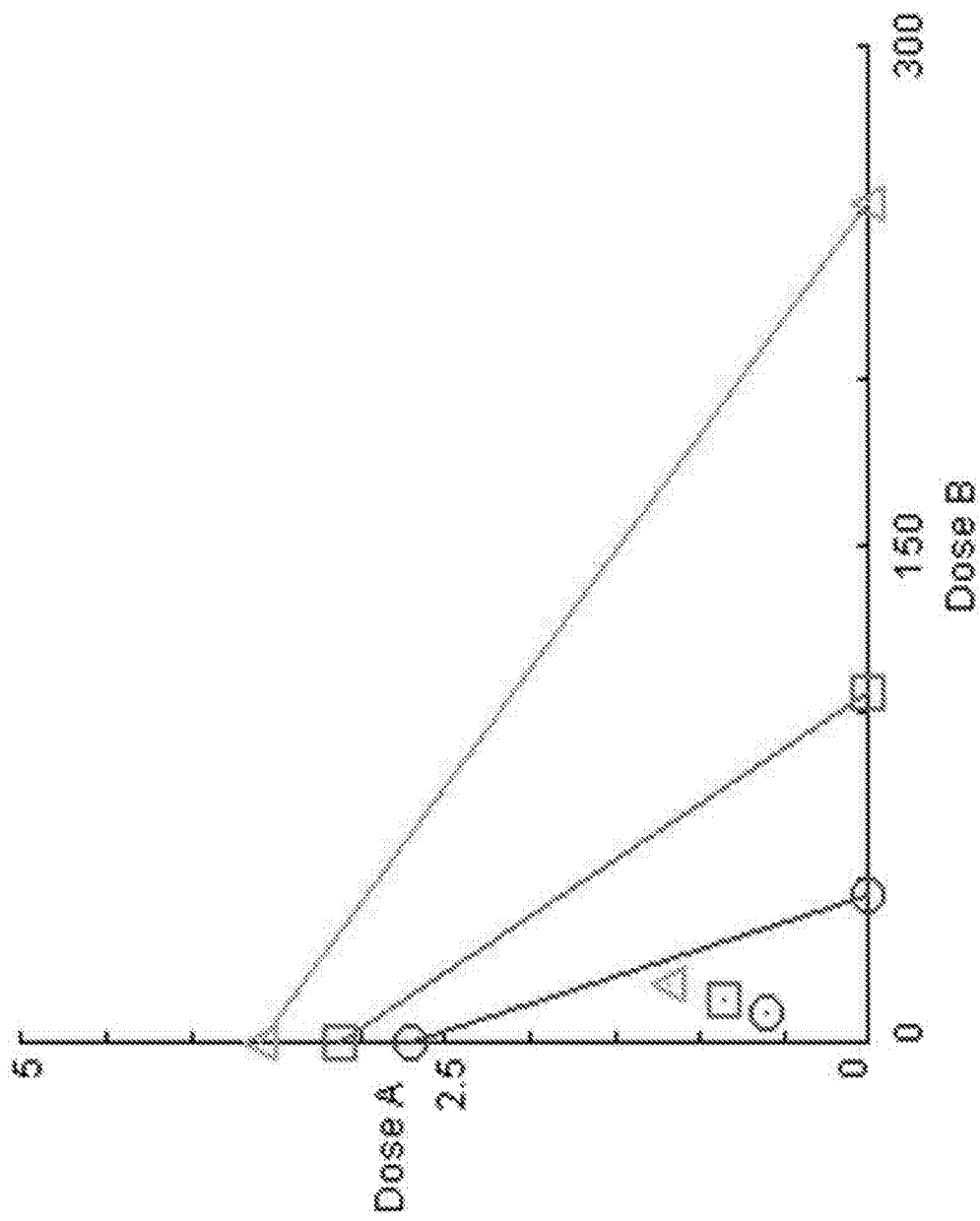
FIG. 16 is a classical isobologram plot for three combinational doses of CMX-020 and Duloxetine in a rodent model of Chemotherapeutic induced pain.
Figure 17:
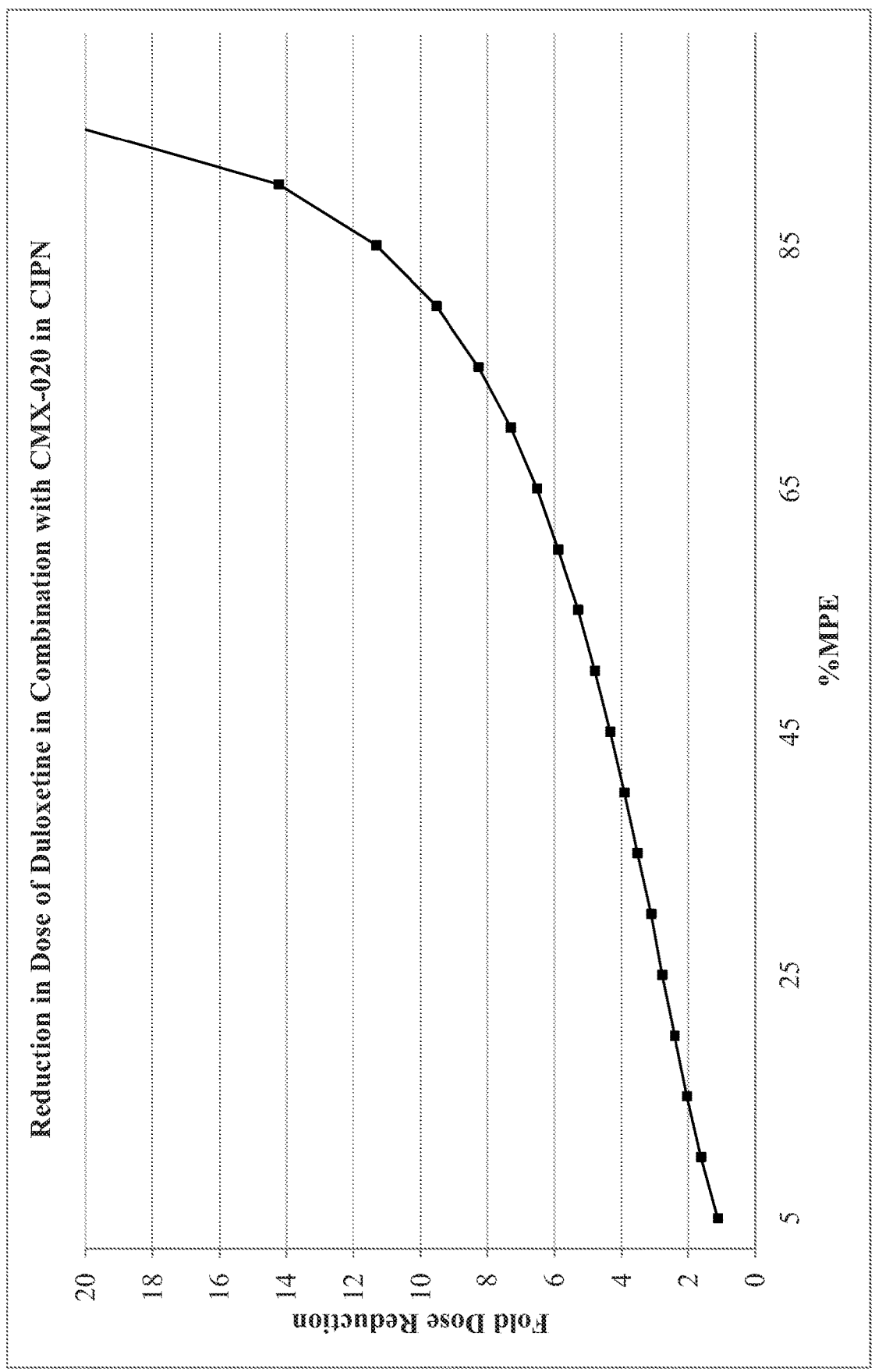
FIG. 17 is a graph showing fold dose reduction of the Duloxetine dose as a function of analgesic effect of CMX-020 (% MPE) in a rodent model of Chemotherapeutic induced pain.

Example 13: Co-Administration of CMX-020 and Duloxetine Produces a Synergistic Analgesic Effect in a Rodent Model Chemotherapeutic Induced Pain In FIGS. 16 and 17, groups of male Sprague Dawley rats received four daily consecutive injections of paclitaxel (1 mg/kg, ip), followed by a second series of four daily injections one week after the first injection, inducing a model of chemotherapeutic-induced peripheral neuropathy Animals were tested 2-3 days after receiving the last injection of paclitaxel with treatment of CMX-020 and Duloxetine administered either alone or in combination at various combinational doses and efficacy was tested using mechanical allodynia pain thresholds (Von Frey Filaments, up-down method). The method of Chou-Talalay and CompuSyn computer software were used to automate analysis of dose effect data for each individual drug and their combination. Using a classical isobologram plot (FIG. 16), it shows that the analgesic effect of the combinational therapy is greater than a simple additive effect i.e., below the "line of additivity" (Dose A=CMX-020, Dose B=Duloxetine). The fold reduction of Duloxetine in combination with CMX-020 is greater than 2-fold in efficacy ranges at and greater than 20% (FIG. 17).

Figure 18:
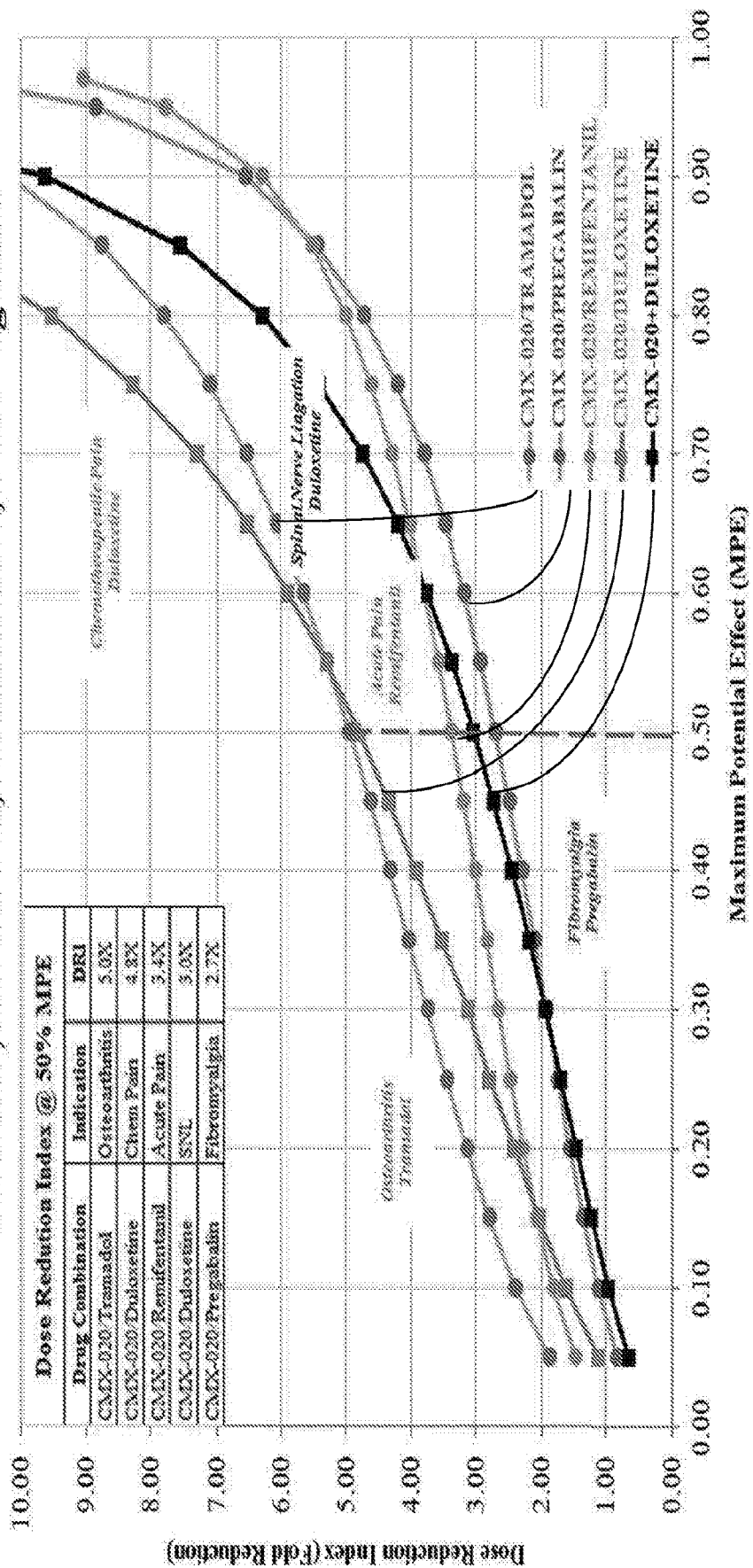
FIG. 18 is a graph showing oral CMX-020 at various therapeutic levels and fold dose reduction for Tramadol, Duloxetine, Remifentanil as a function of analgesic effect of CMX-020 (% MPE)

Example 14: Co-Administration of CMX-020 and Other Pain Therapeutics Produces a Synergistic Analgesic Effect in Neuropathic Pain Animal Models, CMX-020 as a Platform Drug In summary, as shown in examples 9-13 the co-administration of CMX-020 and other pain therapeutics i.e., Duloxetine, Tramadol, Remifentanil and Pregabalin produces a synergistic analgesic effect in various animal models of neuropathic pain even at low effect levels. This combinational effect may provide reduced total drug exposure to each active ingredient while maintaining or exceeding the total therapeutic effect of each active alone. In addition, the reduction of each active dose may potentially reduce side effects attributed to either drug. FIG. 18, summaries the dose reduction index (DRI) plots for other drugs in combination with CMX-020 that have been experimentally determined. Values above 2 DRI indicate synergistic effects in which the doses of drugs may be reduced lower than required when compared to a simple additive effect.

Example 15: The Delivery Vehicle Provides a Flexible Environment for Combining CMX-020 with Other Synergistic Pain Therapeutics, which May not be Soluble in Fish Oil Options:

(1) If the second drug is a liquid, but not miscible with CMX-020/DHA TG or is soluble in water, then a combination of the second drug alone or in water, as appropriate, plus CMX-020/DHA TG will be converted into an emulsion. An emulsion is a mixture of two or more liquids that are normally immiscible (unmixable or unblendable). In an emulsion, one liquid (the dispersed phase) is dispersed in the other (the continuous phase). Examples of emulsions include vinaigrettes, milk, and mayonnaise. Two liquids can form different types of emulsions. Oil and water, for example, can lead to an oil-in-water emulsion, wherein the oil is the dispersed phase, and water is the dispersion medium. Alternatively, they can form a water-in-oil emulsion, wherein water is the dispersed phase and oil is the external phase. Multiple emulsions are also possible, including a "water-in-oil-in-water" emulsion and an "oil-in-water-in-oil" emulsion. The resultant emulsion could offer some additional protection to the CMX-20 and second drug from autooxidation and extend their shelf-life.

(2) If the second drug is a solid, the particle size will be reduced by any of a variety of extant techniques and used to form a colloid or nanosuspension in the CMX-20/DHA TG vehicle. Typically, the dispersed particles have an average diameter of anywhere from 1 to 1000 nanometers.

(3) The new drug will be dissolved in a small amount of a solvent (e.g., ethanol) that is compatible with the fish oil and softgel capsule. The two solutions will be combined, and concentrations and chemistries adjusted to ensure that the new drug does not separate or precipitate.

Figure 19:
FIG. 19 is a representative chemical formula showing the new drug as a salt and replacing the gegenion or counterion with a lipid soluble ion.

(4) The new drug will be modified to generate a pro-drug to improve its solubility in fish oil. For instance, if the new drug has an alcohol, it will be derivatized to make the DHA ester. Or, if the new drug is a salt, replace the gegenion or counterion with something lipid soluble, e.g., replace a sodium cation with tetrabutylammonium cation. See FIG. 19.

Dual Release Formulation

Figure 20A:
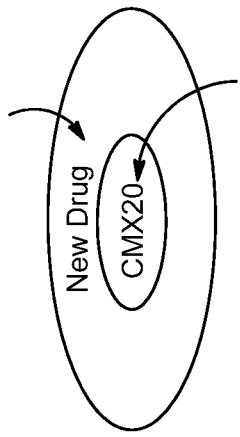
FIG. 20A is a schematic of a dual release formulation with CMX-020 encapsulated by a new drug.

In its current formulation, CMX-020 is released after it passes through the stomach and is absorbed in the remaining GI tract. This might be acceptable for other drugs as well. However, some drugs are best absorbed from the stomach. In this situation, a two-stage release might be desirable, i.e., the new drug is released as it passes through the stomach and CMX-020 is only released afterwards. One (or more) smaller softgel is inside of a larger softgel as seen in FIG. 20A.

Figure 20B:
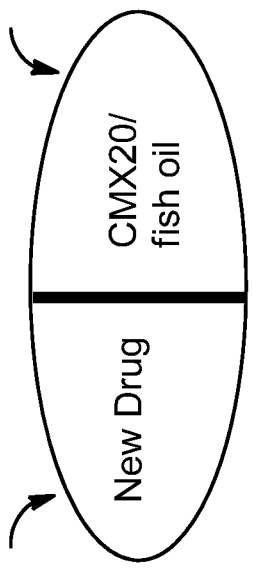
FIG. 20B is a schematic of the dual release formulation with CMX-020 side by side with the new drug.

Of course, there are other possible configurations such as side by side compartments as seen in FIG. 20B.

REFERENCES

Müller, R. H., C. Jacobs, and O. Kayser. "Nanosuspensions as particulate drug formulations in therapy: rationale for development and what we can expect for the future." *Advanced drug delivery reviews* 47.1 (2001): 3-19.

Leuner, Christian, and Jennifer Dressman. "Improving drug solubility for oral delivery using solid dispersions." *European journal of Pharmaceutics and Biopharmaceutics* 50.1 (2000): 47-60.

Example 16: Delivery Vehicle Delivers CMX-020 in Human Clinical Study

In early 2015, oral CMX-020 was evaluated for safety, tolerability and pharmacokinetics in a Phase 1 clinical trial conducted under Cytometix Protocol CMX020-O-02-14-001-A2 [2015] at Cmax (IDT), in Adelaide, Australia. Cohorts of healthy male and female subjects aged 18-50 were evaluated. Each cohort included 8 subjects, 4 males and 4 females received CMX-020. FIG. 18 and Table 6 below show CMX-020 PK levels for a single dose at 50 mg and at 100 mg after 5 days of BID (twice a day) dosing with each dose level. Oral CMX-020 therapeutic levels, which are associated with PK levels above 40 ng/ml, are shown between 4-8 hours with Tmax between 3.5-5.5 hours after dosing. The CMX-020 oral investigational drug product is comprised of a solution of 5% (w/w) CMX-020 containing ~3000 ppm mixed tocopherols in purified DHA triglycerides encapsulated in an enterically coated softgel. The fill formulation for the drug product in this study contains 10 mg of CMX-020.

CMX-020 Drug Product Fill Formulation for Clinical Study

TABLE 6

| Component | Grade | Function | Quantity/Softgel |
|---|---|---|---|
| CMX-020/AVACAT | Inhouse | Active Ingredient | 10 mg |
| Purified DHA | cGMP | Solubilizer and Stabilizer | 190 mg |
| Mixed Tocopherols | USP | Anti-oxidant | ~3000 ppm |

Figure 21:
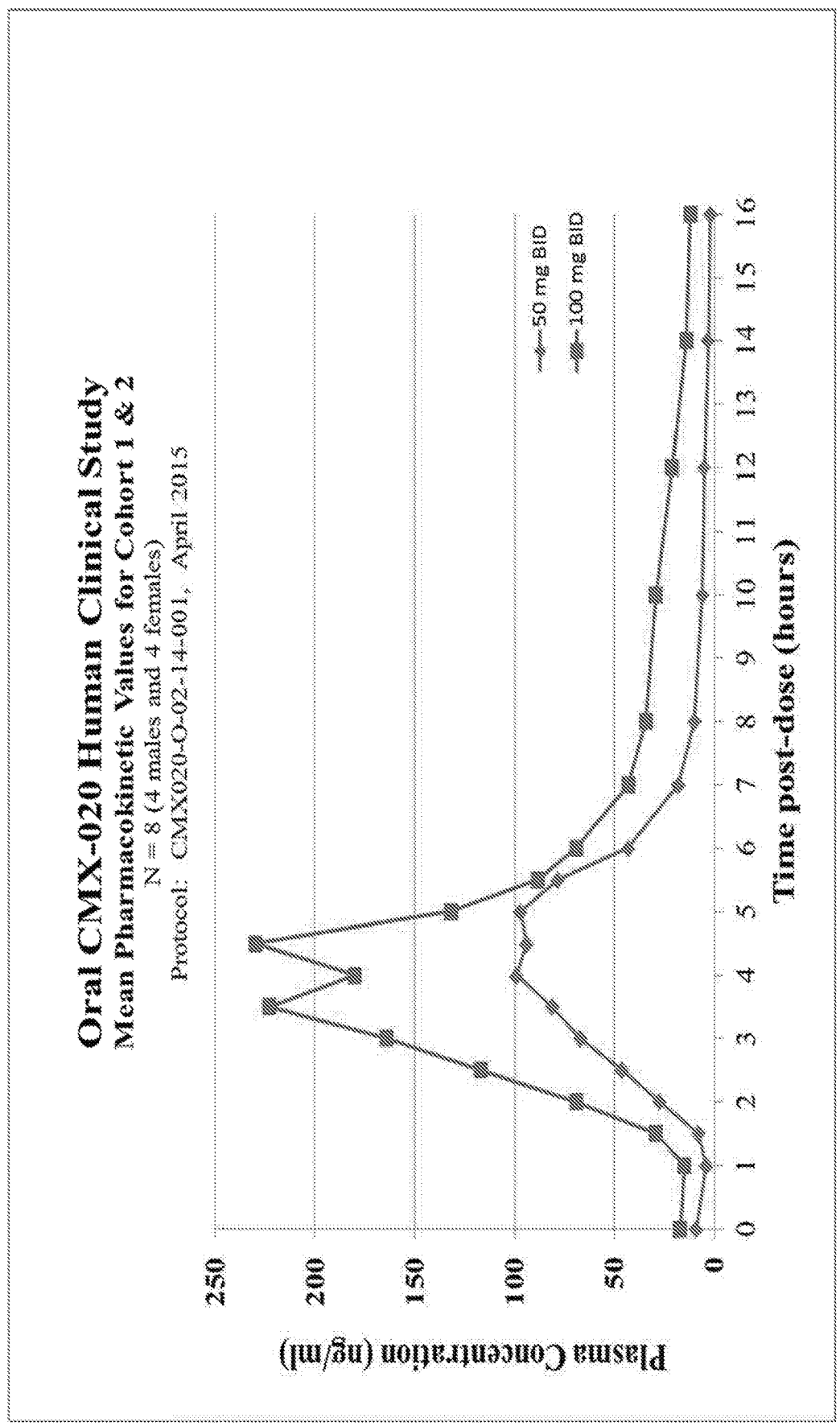
FIG. 21 is a graph showing CMX-020 plasma concentration measured over time for two cohorts under BID (twice a day) dosing conditions.

FIG. 21 illustrates the time course profile for two cohorts under BID dosing conditions. These profiles indicate a dose-dependent increase in CMX-020 plasma concentrations for both cohorts. The peak time of plasma concentration (Tmax) of CMX-020 is consistent for both cohorts. Both Cmax and drug exposure (as defined by AUClast) for BID doses show predictable dose proportionality: $r^2=0.9923$ and $r^2=0.9275$, respectively.

Other embodiments and uses of the invention will be apparent to those skilled in the art from consideration from the specification and practice of the invention disclosed herein. All references cited herein for any reason, including all journal citations and U.S./foreign patents and patent applications, are specifically and entirely incorporated herein by reference. It is understood that the invention is not confined to the specific reagents, formulations, reaction conditions, etc., herein illustrated and described, but embraces such modified forms thereof as come within the scope of the following claims.

We claim:
1. An oral delivery system, comprising:
   a. an enteric coated softgel; and
   b. a liquid formulation contained within the enteric coated softgel, the liquid formulation including a vehicle comprising:
      i. a combination of purified docosahexaenoic acid (DHA) and purified eicosapentaenoic acid (EPA) in triglyceride forms; and
      ii. optionally, one or more of an antioxidant, a surfactant, a solubilizer, a stabilizer, a lubricant, or a pH/tonicity adjustment agent; and
      iii. a therapeutic that is CMX-020
   wherein the vehicle comprises a combination of about 50% (w/w) DHA in triglyceride form and about 32% (w/w) EPA in triglyceride form; and
   wherein the CMX-020 is about 2-25% (w/w) of the liquid formulation.

2. The oral delivery system of claim 1, wherein the antioxidant is selected from the group consisting of a mixed tocopherol, a pure tocopherol, a carotene, a propyl gallate, a butylated hydroxytoluene (BHT), a butylated hydroxyanisole (BHA), and combinations thereof.

3. The oral delivery system of claim 1, wherein the CMX-020 is about 5% (w/w) of the liquid formulation.

4. The oral delivery system of claim 1, wherein the composition comprises a second therapeutic.

5. The oral delivery system of claim 1, wherein the composition comprises a second therapeutic selected from a group consisting of remifentanil, pregabalin, tramadol, duloxetine, and a combination thereof.

6. The oral delivery system of claim 4, wherein the second therapeutic is contained in a non-enteric coated outer shell surrounding the enteric coated softgel.

7. The oral delivery system of claim 6, wherein the outer shell releases the second therapeutic in a simulated gastric fluid test solution in less than about 2 hours.

8. A method of delivering an effective dosage of a therapeutic to a patient to treat pain, comprising administering the oral delivery system according to claim 1 to the patient in need thereof, wherein the effective dosage of the therapeutic contained within the oral delivery system is delivered to said patient.

* * * * *